United States Patent
Ellis et al.

(10) Patent No.: US 7,749,512 B2
(45) Date of Patent: Jul. 6, 2010

(54) PORCINE *HELICOBACTER* INFECTION

(75) Inventors: John Ellis, Saskatoon (CA); George Krakowka, Colombus, OH (US); Kathryn Eaton, Saline, MI (US); Joel Flores, Mechanicsville, VA (US)

(73) Assignee: Cerebus Biologicals Inc., Laramie, WY (US)

( * ) Notice: Subject to any disclaimer, the term of this patent is extended or adjusted under 35 U.S.C. 154(b) by 76 days.

(21) Appl. No.: 11/360,366

(22) Filed: Feb. 23, 2006

(65) Prior Publication Data

US 2007/0025916 A1 Feb. 1, 2007

Related U.S. Application Data

(63) Continuation-in-part of application No. 11/196,722, filed on Aug. 3, 2005, now abandoned, which is a continuation-in-part of application No. PCT/US04/02867, filed on Feb. 2, 2004.

(60) Provisional application No. 60/444,190, filed on Feb. 3, 2003, provisional application No. 60/518,156, filed on Nov. 7, 2003, provisional application No. 60/655,965, filed on Feb. 23, 2005.

(51) Int. Cl.
*A61K 39/02* (2006.01)
(52) U.S. Cl. .................................. 424/234.1

(58) Field of Classification Search ....................... None
See application file for complete search history.

(56) References Cited

OTHER PUBLICATIONS

D. De Groote et al: "Detection of "Candidatus Helicobacter suis" in gastric samples of pigs by PCR: comparison with other invasive diagnostic techniques.", Journal of Clinical Microbiology Mar. 2000, vol. 38, No. 3, Mar. 2000, pp. 1131-1135, XP002408281.
K.A. Eaton et al.: "Vccination of Gnotobiotic Piglets against *Helicobacter pylori*", Department of Veterninary Biosciences, Ohio State University, Columbus, Nov. 1998, vol. 178, pp. 1399-1405.

*Primary Examiner*—Robert B Mondesi
*Assistant Examiner*—Brian J Gangle
(74) *Attorney, Agent, or Firm*—Judy Jarecki-Black; Chad Kitchen; Merial Limited

(57) ABSTRACT

Compositions and methods for treating, preventing and diagnosing *Helicobacter* infection are disclosed. The methods use proteins and/or nucleic acids derived from *Helicobacter cerdo*, a new pathogen isolated from swine. In addition, porcine models for studying bacterial gastritis and gastric and duodenal ulcer disease caused by *Helicobacter* pathogens, such as *H. pylori* and *H. cerdo* are described, as well as methods of identifying vaccines and compounds for treating and/or preventing *Helicobacter* infection using the animal models. Also described are methods of preventing *Helicobacter* infection in swine, such as infection caused by *H. cerdo*, using immunogenic proteins and nucleic acids derived from *Helicobacter* pathogens, such as *H. pylori*.

3 Claims, 5 Drawing Sheets

Fig. 2

PORCINE *HELICOBACTER* INFECTION

CROSS-REFERENCE TO RELATED APPLICATIONS

This application is a continuation-in-part of U.S. application Ser. No. 11/196,722, filed Aug. 3, 2005 now abandoned, which is a continuation-in-part of International Application No. PCT/US2004/002867, filed Feb. 2, 2004, published as WO 2004/069184 on Aug. 19, 2004, and claiming priority to U.S. applications Ser. Nos. 60/444,190 and 60/518,156, filed Feb. 3, 2003 and Nov. 7, 2003, respectively. This application also claims priority to U.S. application Ser. No. 60/655,965, filed Feb. 23, 2005.

All of the foregoing applications, as well as all documents cited in the foregoing applications ("application documents") and all documents cited or referenced in the application documents are incorporated herein by reference. Also, all documents cited in this application ("herein-cited documents") and all documents cited or referenced in herein-cited documents are incorporated herein by reference. In addition, any manufacturer's instructions or catalogues for any products cited or mentioned in each of the application documents or herein-cited documents are incorporated by reference. Documents incorporated by reference into this text or any teachings therein can be used in the practice of this invention. Documents incorporated by reference into this text are not admitted to be prior art.

FIELD OF THE INVENTION

The present invention relates generally to bacterial pathogens. In particular, the invention pertains to animal models for studying bacterial gastritis and gastric and duodenal ulcer disease, such as caused by *Helicobacter pylori* and *Helicobacter cerdo*, as well as methods of treating and preventing *Helicobacter* infection in swine, such as infection caused by *H. cerdo*, using immunogenic proteins and nucleic acids derived from *Helicobacter* pathogens such as *H. pylori*.

BACKGROUND

Gastric disease is an important cause of morbidity and economic loss in swine-rearing operations (O'Brien, J. (1992) "Gastric ulcers" p. 680. In A. D. Leman, B. E. Straw, W. L. Mengeling, and S. D. D'Allaire (ed), *Diseases of swine*. Wolfe, London, United Kingdom). Although the cause of porcine gastric disease has not been previously established, it is most often attributed to diet and/or stress (O'Brien, J. (1992) "Gastric ulcers" p. 680. In A. D. Leman, B. E. Straw, W. L. Mengeling, and S. D. D'Allaire (ed), *Diseases of swine*. Wolfe, London, United Kingdom).

In 1984, *Helicobacter pylori* (Hp) emerged as an etiologic agent in human gastritis/ulcer disease following the documentation of this agent in patients with gastritis (Marshall and Warren (1984) *Lancet* 1:1311-1314). Hp is a Gram-negative microaerophilic urease-positive small curved rod-shaped bacterium which possesses several unusual characteristics related to its gastric ecological niche. The hallmark for the members of the *Helicobacter* genus is expression of urease enzyme. The presence of this enzyme and its activity in the hydrolysis of urea forms the basis of presumptive tests (urea breath test and others) for gastric colonization. The organism colonizes the mucus layer of the gastric cardia and antrum and infection is presumed to be lifelong.

Hp is now universally recognized as one of the primary gastric pathogens, and the study of this bacterial species and the spectrum of diseases associated with it has become a major focus in human gastroenterology (Suerbaum and Michetti (2002) *N. Eng. J. Med.* 347:1175-1186). Hp is causally associated with chronic superficial (active) type B gastritis (Buck (1990) *Clin. Micro. Rev.* 3:1-12; Blaser (1992) *Gasteroenterol.* 102:720-727; Consensus Statement, 1994, NSAID), independent gastric ulceration (Peterson (1991) *N. Eng. J. Med.* 324:1043-1047; Moss and Calam (1992) *Gut* 33:289-292; Leung et al. (1992) *Am. J. Clin. Pathol.* 98:569-574; Forbes et al. (1994) *Lancet* 343:258-260), atrophic gastritis (Nomura et al. (1991) *N. Engl. J. Med.* 325:1132-1136; Parsonnet et al. (1991) *JNCI* 83:640-643; Sipponen (1992) *Drugs* 52:799-804, 1996), and gastric MALT lymphoma (Rodriguez et al. (1993) *Acta Gastro-Enterol. Belg.* 56(suppl):47; Eidt et al. (1994) *J. Clin. Pathol.* 47:436-439). Additionally, atrophic gastritis and resultant acholrhydria is now thought to represent the last stage in the progression of persistent lifelong colonization by Hp (Leung et al. (1992) *Am. J. Clin. Pathol.* 98:569 574).

Early attempts to reproduce disease with Hp were frustrated because commonly used laboratory animal species were found to be highly resistant to Hp gastric colonization. Experimental animal models of Hp gastritis infection have since been developed. Prominent among these is the gnotobiotic piglet model for acute bacterial gastritis (Krakowka et al. (1987) *Infect. Immun.* 55:2789-2796). Gnotobiotic swine, as monogastric omnivores whose gastric anatomy and physiology most closely replicates humans (Bertram et al. (1991) *Rev. Infect. Dis.* 13:S714-S722), are susceptible to oral colonization with many different Hp strains (Krakowka et al. (1987) *Infect. Immun.* 55:2789-2796; Bertram et al. (1991) *Rev. Infect. Dis.* 13:S714-S722). Lewis antigenic arrays expressed on human mucoproteins and cell surface glycoproteins are thought to be binding receptors for Hp bacterial lipopolysaccharide and other surface glycoproteins (Vandenbroucke-Grauls et al. (1998) *Ital. J. Gastroenterol. Hepatol.* 30:259-260). Swine gastric tissues, unlike other laboratory animal species except primates are also Lewis antigen-positive (Appelmelk et al. (1998) "Molecular Mimicry between *Helicobacter pylori* and the host" in *Helicobacter pylori: Basis Mechanisms to Clinical Cure* (1998) R. H. Hunt, Tytgat G N T, eds.).

Of the domestic animal species, swine are the most commonly affected with clinically significant gastric ulcers (O'Brien J. J. Gastric Ulcers. *Diseases of Swine*, 6th ed. Editors A D Leman A D, et al., (1986), 680-691; Embaye et al. (1990) *J. Comp. Path.* 103:253-264). In modern swine-intensive production systems, the development of ulcers and erosions of the nonglandular esophageal (cardiac) gastric lining and antral gastric mucosa is a common and serious disease problem (O'Brien J. J. Gastric Ulcers. *Diseases of Swine*, 6th ed. Editors A D Leman A D, et al., (1986), 680-691). A prevalence of 5-100% for gastroesophageal ulcerations (GEU) is reported, death losses from fatal hemorrhages of 3% or more are reported (O'Brien J. J. Gastric Ulcers. *Diseases of Swine*, 6th ed. Editors A D Leman A D, et al., (1986), 680-691; Embaye et al. (1990) *J. Comp. Path.* 103:253-264) and sublethal economic losses are substantial.

Porcine gastric mucosal ulceration and GEU are attributed to reflux of acidic gastric contents onto the unprotected pars esophagea (Argenzio et al. (1975) *Am. J. Physiol.* 228:454-462; Argenzio et al. (1996) *Am. J. Vet. Res.* 57:564-573). In particular, the stratified squamous epithelium of the pars esophagea is devoid of mucous-producing glands and lacks the sodium bicarbonate buffering system characteristic of the gastric glandular mucosa and, as a consequence, the pars is frequently damaged by the acidic contents of the stomach.

Elevated gastric acid content is multifactorial and thought to be largely due to a combination of excess parietal cell production of hydrochloric acid, luminal hydrolysis of luminal carbohydrate, both coupled with a loss of pH gradient in the stomachs of swine fed a finely ground low roughage high carbohydrate diet.

Feeder swine diets contain unsaturated fatty acids, short chain (acetate, propionate, butyrate and lactate) free fatty acids or peroxidized fats, all of which elevate luminal acid concentration (Argenzio et al. (1975) *Am. J. Physiol.* 228: 454-462). Finishing diets high in carbohydrate such as corn and cornstarch are also a primary dietary source of acidic metabolites in pigs. Incomplete glycolysis of cornstarch by parietal cell-origin hydrogen ions and/or enzymatic actions of commensal fermentative microbes such as the *Lactobacillus* and *Bacillus* spp. results in the generation of lactic, acetic and propionic acids within the gastric compartment. Indeed it has been demonstrated that gastric colonization with fermentative bacterial species resulted in GEU if a dietary source of carbohydrate (corn syrup) was provided to colonized gnotobiotes (Krakowka et al. (1998) *Vet. Pathol.* 35:274-282). Finally, in feeder swine, the physical form of diet also influences development of GEU (O'Brien J. J. Gastric Ulcers. *Diseases of swine,* 6th ed. Editors A D Leman A D, et al., (1986), 680-691). In general, a finely ground (<3.5 mesh) diet, even in pelleted form is an important risk factor for ulcerogenesis presumably because of the general inability of these diets to "confine" released acids to the fermentation compartment of the glandular stomach. The loss of a pH gradient associated with finely ground diets permits cranial acid reflux into the pars esophagea.

As in humans with recurrent "heart burn," reflux esophagitis and Barrett's esophagus, it is believed that gastric-origin hydrogen ions and acidic metabolites of partial intragastric glycolysis enter and acidify the squamous epithelial cell cytoplasm. The cell membrane-bound Na—K-ATPase is disrupted which results in accumulation of intracellular sodium ions and secondary accumulation of intracellular water, recognized histologically as acute cellular swelling, hydropic degeneration, epithelial parakeratosis and ultimately necrosis. For erosive lesions, the underlying basement membrane remains intact and re-epithelization of the damaged portion of the pars is rapid. Presumably pivotal to progression of epithelial erosions to ulceration is penetration of the basement membrane and continued acid-mediated damage to the underlying lamina propria. This devitalized tissue may be secondarily colonized by commensal microbes including fermentative anaerobes. In humans as well as swine, there is a strong consensus that a relative or absolute increase in gastric hydrogen ions (acid) is the proximate cause of pars and esophageal damage. Thus, a therapeutic goal in humans is to elevate gastric pH towards neutrality through the use of bicarbonate buffering medications and to inhibit new gastric hydrogen ion production by parietal cells of the gastric fundus with proton pump inhibitors. These over-the-counter medications provide immediate symptomatic relief for patients affected with heart burn and reflux esophagitis and indirectly implicate gastric hyperacidity in the pathogenesis of disease. However, such medications do not cure the underlying cause of the disease.

Attempts to treat Hp infection in humans using immunotherapy rather than chemotherapy has been largely unsuccessful. In particular, induction of immunity which mimics the "natural" immune response of convalescent infected humans has not been successful, since human Hp infection can persist indefinitely in spite of a strong immune response to Hp (Lee (1996) *Gastroenterol.* 110:2003-2006). In mice, protection has been achieved with sonicates or recombinant proteins such as ureA and ureB, vacA and GroEL, given orally with cholera toxin (CT) and heat labile toxin (LT) as adjuvants. The focus has been primarily upon the use of purified and/or recombinant bacterial proteins as target immunogens in vaccine development programs. In general, inconsistent and only partial protection has been achieved. In rodent systems, mucosal vaccination assisted by CT or LT has emerged as the favored route, notwithstanding the fact that these species are highly resistant to toxic effects of CT/LT and the resultant rodent data does not directly translate into the human or swine experience.

In particular, in piglets immunized and then challenged with Hp, the strongest pre-challenge indicator of efficacy is the level and presence of Hp-specific serum/salivary IgG, not IgA (Eaton and Krakowka (1992) *Gastroenterol.* 103:1580-1586). Parenteral vaccination stimulates a strong IgG response; oral vaccination does not. Parenteral immunization was completely protective in 50% of the piglets immunized subcutaneously and in 60% of piglets immunized intraperitoneally (Eaton et al. (1998) *J. Infect. Dis.* 178:1399-1405). In contrast, oral vaccination with: 1) live bacteria (cleared with antimicrobials prior to challenge), 2) whole intact killed bacteria, 3) whole bacterial sonicates and 4) whole bacterial sonicates with mucosal LT adjuvant failed to provide a single instance (0 of 27 piglets or 0%) of protection. Bacterial cfu were reduced compared to controls but the levels of reduction did not reach statistical significance. Thus, in the porcine model of Hp colonization and acute gastritis, the parenteral route of vaccination appears to be superior to the oral route in both absolute (infected versus uninfected after challenge) and relative (bacterial cfu in vaccinates versus nonvaccinated controls) measures of antimicrobial efficacy.

Multiple agent antimicrobial therapies have been available for human Hp for more than a decade. These therapies can be expensive, cumbersome to administer, and often do not completely cure the disease. Such therapies would be impractical in domestic livestock. Moreover, injudicious use of antimicrobials promotes emergence of antibiotic-resistant strains of Hp and Hp resistance to metronidazole and clarirythromycin has increased (Michetti, (1997) *Gut* 41:728-730). Additionally, the use of antibiotics in food animals is undesirable. Thus, there is a continuing need for discovering new modes of preventing or treating *Helicobacter* infection in both humans and animals. Animal models that mimic *Helicobacter* infection are of great use in studying treatment and prevention options.

Recently, a new *Helicobacter* pathogen was recovered from swine exhibiting gastritis/ulcer disease. This pathogen, named *H. cerdo*, has been shown to cause gastric disease in young piglets that is similar to Hp-associated active gastritis in humans.

SUMMARY OF THE INVENTION

The present invention is based on the discovery of a novel *Helicobacter* pathogen isolated from swine exhibiting gastritis/ulcer disease. This organism has been named *Helicobacter cerdo* (Hc) by the inventors herein. This organism has been shown by the inventors to cause gastric disease in young piglets that is similar to Hp-associated active gastritis in humans.

Subunit vaccines, including antigens and mixtures of antigens derived from *H. cerdo*, provide protection against subsequent infection with *Helicobacter* species, such as *H. pylori* and *H. cerdo*. The present invention provides a safe, efficacious and economical method of treating and/or preventing Hc infection in swine.

Accordingly, in one embodiment, the invention is directed to a composition comprising a pharmaceutically acceptable vehicle and at least one *H. cerdo* immunogen. In certain embodiments, the at least one *H. cerdo* immunogen is provided in an *H. cerdo* lysate, such as a lysate produced by proteolytic digestion of *H. cerdo* bacteria. In additional embodiments, the composition further comprises an adjuvant.

In another embodiment, the invention is directed to methods of treating or preventing a *Helicobacter* infection in a vertebrate subject comprising administering to the subject a therapeutically effective amount of a composition as described above. In certain embodiments, the vertebrate subject is a porcine subject. In additional embodiments, the *Helicobacter* infection is an *H. cerdo* infection. In yet further embodiments, the composition is administered parenterally.

In yet another embodiment, the invention is directed to methods of treating or preventing an *H. cerdo* infection in a porcine subject comprising parenterally administering to the subject a therapeutically effective amount of a composition as described above.

In another embodiment, the invention is directed to a method of producing a composition comprising providing at least one *H. cerdo* immunogen; and combining the *H. cerdo* immunogen with a pharmaceutically acceptable vehicle.

In certain embodiments, the at least one *H. cerdo* immunogen is provided in an *H. cerdo* lysate, such as an *H. cerdo* lysate produced by proteolytic digestion of *H. cerdo* bacteria. In additional embodiments, an adjuvant is also provided.

In yet another embodiment, the invention is directed to a method of detecting *Helicobacter* infection in a subject comprising providing a biological sample from the subject; and reacting the biological sample with at least one *H. cerdo* immunogen, under conditions which allow *Helicobacter* antibodies, when present in the biological sample, to bind with the immunogen(s), thereby detecting the presence or absence of *Helicobacter* infection in the subject.

In certain embodiments, the method further comprises removing unbound antibodies; providing one or more moieties capable of associating with the bound antibodies; and detecting the presence or absence of the one or more moieties, thereby detecting the presence or absence of *H. cerdo* infection.

In certain embodiments, the detectable label is a fluorescer or an enzyme. In additional embodiments, the at least one immunogen is provided in an *H. cerdo* lysate. In still further embodiments, the biological sample is a porcine serum sample.

In additional embodiments, the invention is directed to a method of detecting *H. cerdo* infection in a porcine subject comprising providing a biological sample from the subject; and reacting the biological sample with at least one *H. cerdo* immunogen, under conditions which allow *H. cerdo* antibodies, when present in the biological sample, to bind with the immunogen(s); removing unbound antibodies; providing one or more moieties capable of associating with the bound antibodies; and detecting the presence or absence of the one or more moieties, thereby detecting the presence or absence of *H. cerdo* infection.

In still further embodiments, the invention is directed to an antibody specific for a *H. cerdo* immunogen. In certain embodiments, the antibody is a polyclonal antibody. In other embodiments, the antibody is a monoclonal antibody.

In another embodiment, the invention is directed to a *H. cerdo* lysate comprising at least one *H. cerdo* immunogen. In certain embodiments, the *H. cerdo* lysate is produced by proteolytic digestion of *H. cerdo* bacteria.

The present invention is also based on the discovery of animal models that mimic human *H. pylori* infection as well as porcine *Helicobacter* infection. The animal models consist of gnotobiotic piglets that are immunized with vaccine candidates and then challenged with *H. cerdo* or *H. cerdo*-like bacteria. In some embodiments, the piglets are inoculated with *H. cerdo* and optionally fed a milk-replacement diet containing a dietary source of fermentable carbohydrate in order to simulate porcine gastroesophageal ulceration (GEU). The animal models are useful for identifying compounds and compositions, such as *H. pylori* and *H. cerdo* vaccine candidates, that have the ability to prevent or treat *Helicobacter* infection in humans and animals, such as swine.

Accordingly, in one embodiment, the invention provides a method for infecting a gnotobiotic piglet with a porcine isolate of *H. cerdo*, the method comprising isolating *H. cerdo* from a porcine subject to produce an *H. cerdo* isolate and administering the *H. cerdo* isolate to the piglet in an amount of sufficient to cause *H. cerdo* infection in the piglet.

In another embodiment, the invention provides a method for evaluating the ability of a vaccine to prevent *H. cerdo* infection in a pig comprising administering a candidate vaccine to a gnotobiotic piglet; administering an *H. cerdo* isolate to the piglet in an amount sufficient to cause *H. cerdo* infection in an unvaccinated subject; and evaluating the presence of *H. cerdo* infection in the piglet, thereby evaluating the ability of the candidate vaccine to prevent *H. cerdo* infection.

In a preferred embodiment, the candidate vaccine is an *H. pylori* vaccine comprising at least one *H. pylori* immunogen. In another preferred embodiment, the candidate vaccine is an *H. cerdo* vaccine comprising at least one *H. cerdo* immunogen.

An additional embodiment provides a method of producing a porcine animal model of gastroesophageal ulceration (GEU) of the pars esophagea, the method comprising isolating *H. cerdo* from a porcine subject to produce an *H. cerdo* isolate; administering the *H. cerdo* isolate to a gnotobiotic piglet in an amount sufficient to cause *H. cerdo* infection in the piglet; and feeding the infected piglet a milk-replacement diet that contains a dietary source of fermentable carbohydrate under conditions sufficient for producing GEU of the pars esophagea.

In a preferred embodiment, the dietary source of fermentable carbohydrate is corn syrup.

A further embodiment provides a method of identifying a compound capable of treating *Helicobacter* infection, the method comprising administering an *H. cerdo* isolate to a gnotobiotic piglet in an amount sufficient to cause an *H. cerdo* infection in the piglet; delivering a compound or series of compounds to the infected piglet; and evaluating *H. cerdo* infection in the piglet relative to an untreated *H. cerdo*-infected gnotobiotic piglet, wherein reduced *H. cerdo* infection in the piglet relative to the untreated piglet identifies a compound capable of treating *Helicobacter* infection.

Another method of identifying a compound capable of treating *H. cerdo* infection comprises providing a porcine animal model of GEU produced by the methods of the invention; delivering a compound or series of compounds to the infected piglet; and evaluating *H. cerdo* infection in the piglet relative to an untreated *H. cerdo*-infected gnotobiotic piglet, wherein reduced *H. cerdo* infection in the piglet relative to the untreated piglet identifies a compound capable of treating *Helicobacter* infection.

In a preferred embodiment, the *H. cerdo* of the disclosed methods is administered orally to the piglet, preferably in an amount of $10^7$-$10^9$ colony forming units.

Also contemplated by the invention is a method of preventing *H. cerdo* infection in a porcine subject comprising administering to the subject a therapeutically effective amount of a composition comprising at least one *Helicobacter* immunogen. In a preferred embodiment, the composition comprises at least one *H. pylori* immunogen. In an especially preferred embodiment, the composition comprises an *H. pylori* lysate. Preferably, the *H. pylori* lysate is produced by proteolytic digestion of *H. pylori* bacteria. The composition advantageously further comprises an adjuvant. Preferably, the composition is administered parenterally.

These and other embodiments of the subject invention will readily occur to those of skill in the art in view of the disclosure herein.

BRIEF DESCRIPTION OF THE DRAWINGS

Various preferred features and embodiments of the present invention will now be described in more detail by way of non-limiting examples and with reference to the accompanying Figures, in which:

FIGS. 2A and 2B show SDS-PAGE separations of intact *H. cerdo* (2A) and an *H. cerdo* digest (2B). An increased amount of low molecular weight material (<) is seen in the digested preparation.

DETAILED DESCRIPTION OF THE INVENTION

Figure 1:
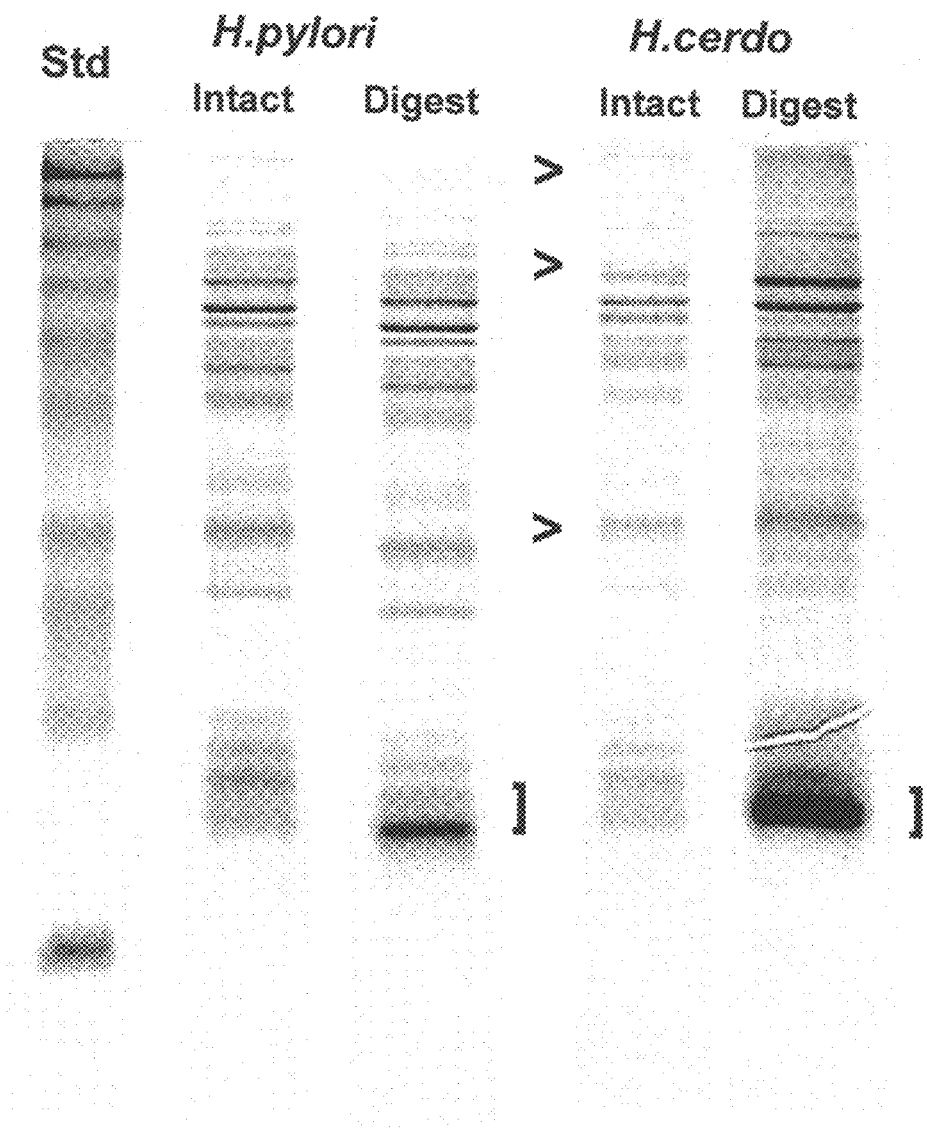
FIG. 1 shows SDS-PAGE profiles of intact and enzymatically digested *H. pylori* and *H. cerdo* lysate preparations, produced as described in the examples. The ">" in the figure illustrates bands present in *H. pylori* and absent from *H. cerdo*. The "]" indicates low molecular weight protease digest products. An increased amount of low molecular weight material is seen in the digested preparations. Both digests stimulated similar antibody responses in pigs when tested using an ELISA.

The practice of the present invention will employ, unless otherwise indicated, conventional techniques of molecular biology, microbiology, bacteriology, recombinant DNA technology, and immunology, which are within the skill of the art. Such techniques are explained fully in the literature. See, e.g., Sambrook, Fritsch & Maniatis, *Molecular Cloning: A Laboratory Manual*, Second Edition (1989); *DNA Cloning*, Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); *Animal Cell Culture* (R. K. Freshney ed. 1986); *Immobilized Cells and Enzymes* (IRL press, 1986); Perbal, B., *A Practical Guide to Molecular Cloning* (1984); the series, *Methods In Enzymology* (S. Colowick and N. Kaplan eds., Academic Press, Inc.); and *Handbook of Experimental Immunology*, Vols. I-IV (D. M. Weir and C. C. Blackwell eds., 1986, Blackwell Scientific Publications).

DEFINITIONS

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "an *H. cerdo* immunogen" includes a mixture of two or more such immunogens, and the like.

By "*Helicobacter* infection" is meant any disorder caused by a *Helicobacter* bacterium, including without limitation, *H. cerdo* ("*H. cerdo* infection"), *H. pylori* ("*H. pylori* infection") and *H. heilmannii* ("*H. heilmannii* infection"), such as, but not limited to, chronic superficial (active) type B gastritis, independent gastric ulceration, peptic, gastric and duodenal ulcers, gastroesophageal ulceration (GEU), proventricular ulcers, ulcerative gastric hemorrhage, atrophic gastritis, and carcinoma including gastric MALT lymphoma. The term also intends subclinical disease, e.g., where *Helicobacter* infection is present but clinical symptoms of disease have not yet manifested themselves. Subjects with subclinical disease can be asymptomatic but are nonetheless at a considerable risk of developing peptic ulcers and/or gastric adenocarcinomas. For a review of *Helicobacter*-associated diseases, see, Telford et al., *Trends in Biotech.* (1994) 12:420-426 and Blaser, M. J., *Scientific American* (February 1996):104-107.

"Evaluating *H. cerdo* infection" or "measuring *H. cerdo* infection" includes examining a piglet for the presence or loss of *H. cerdo* bacteria and/or the development, inhibition, or amelioration of ulcer or tumor formation relative to an untreated *H. cerdo*-infected gnotobiotic piglet. Methods for evaluating or measuring *H. cerdo* infection are taught herein and include gross anatomical observations, observation of histopathologic changes in the gastric and extra-gastric systems, microbiologic studies (including Gram staining, observation of colony morphology, urease and catalase enzyme activity, etc.), immunoreactivity with species-specific antisera and detection of serum antibodies against *Helicobacter* species, and other methods known in the art.

Figure 5B:
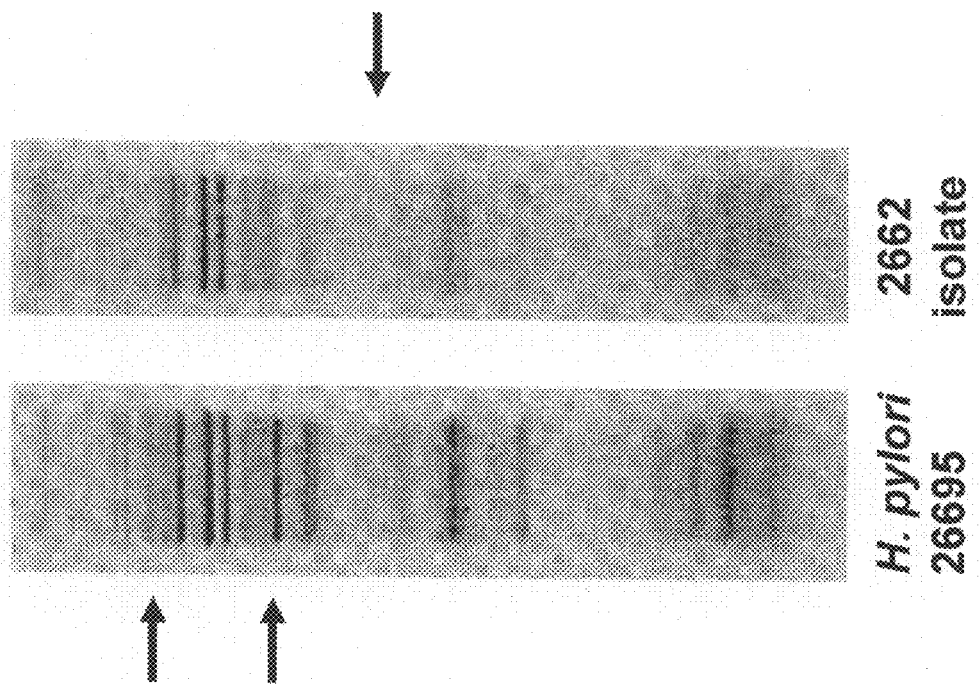
FIGS. 5A and 5B show Coomassie blue-stained (5A) and silver-stained (5B) gels of *H. pylori* isolate 26695 versus *H. cerdo* isolates (2662 and 1268).
Figure 5A:
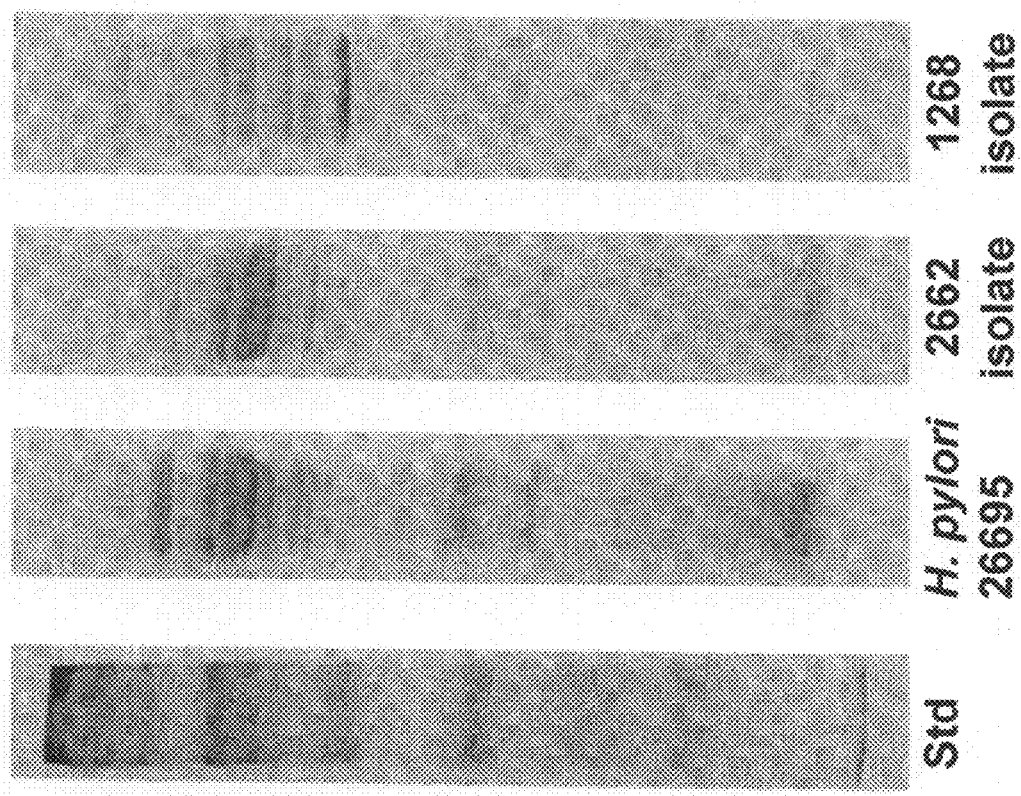

By "*H. cerdo*" is meant a *Helicobacter* pathogen isolated from swine, which has substantially the same properties as *H. cerdo* isolate 2662 as described in the examples below. Thus, the term *H. cerdo* as used herein encompasses porcine *Helicobacter* isolates in addition to isolate 2662. As explained in the examples, isolate 2662 is similar, but not identical to, *H. pylori* pathogens isolated from humans. In particular, *H. pylori* and *H. cerdo* possess the common features characteristic of the *Helicobacter* genus. Thus, an *H. cerdo* pathogen as defined herein has the following characteristics: Gram negative, short curved rods, microaerophilic growth pattern, urease enzyme activity, catalase enzyme activity and possession of the gene cluster referred to as the "cagA pathogenicity island." The protein profile of two *H. cerdo* isolates, 2662 and 1268, are shown in FIG. 5. Moreover, the preferred gastric niche for *H. cerdo* is the lesser curvature of the gastric cardia and the antrum. The former is immediately adjacent to the pars esophagea. As explained in the examples herein, *H. cerdo* isolate 2662 is significantly more pathogenic and ulcerogenic in gnotobiotic pigs than is the archetype human *Helicobacter* species (*H. pylori*, strain 26695). Piglets inoculated with *H. cerdo* isolate 2662 display a higher incidence of erosions and ulcers of the gastric pars (GEU) than piglets infected with *H. pylori*, isolate 1268 or *H. heilmannii*. Additionally, the incidence of ulceration in the glandular mucosa caused by *H. cerdo* isolate 2662 is far greater than seen with *H. pylori*.

By "an *H. pylori* lysate" is meant an extract or lysate derived from an *H. pylori* whole bacterium which includes one or more *H. pylori* immunogenic polypeptides, as defined below. The term therefore is intended to encompass crude extracts that contain several *H. pylori* immunogens as well as relatively purified compositions derived from such crude lysates which include only one or few such immunogens. Such lysates are prepared using techniques well known in the art, described further below.

Representative immunogens that may be present in such lysates, either alone or in combination, include immunogens with one or more epitopes derived from *H. pylori* adhesins such as, but not limited to, *H. pylori* immunogens including a 20 kDa N-acetyl-neuraminillactose-binding fibrillar haemagglutinin (HpaA), a 63 kDa protein that binds phosphatidylethanolamine and gangliotetraosyl ceramide, and a conserved fimbrial pilus-like structure. See, e.g., Telford et al., *Trends in Biotech*. (1994) 12:420-426 for a description of these antigens.

Other immunogens that may be present in the lysate include immunogens with one or more epitopes derived from any of the various *H. pylori* flagellins known as the major flagellin, FlaA and the minor flagellin, FlaB. The flagella of *H. pylori* are composed of FlaA and FlaB, each with molecular weights of approximately 55 kDa. Either or both of FlaA and/or FlaB may be used in the lysates of the present invention.

Another representative *H. pylori* immunogen is an *H. pylori* urease which is associated with the outer membrane and the periplasmic space of the bacterium. The *H. pylori* holoenzyme is a large complex made up of two subunits of 26.5 kDa (UreA) and 61 kDa (UreB), respectively. *H. pylori* immunogens with epitopes derived from the holoenzyme, either of the subunits, or a combination of the three, can be present in the compositions.

Another representative immunogen that may be present in the lysate or used in further purified form includes the *H. pylori* heat shock protein known as "hsp60." See, e.g., International Publication No. WO 93/18150.

Additionally, the *H. pylori* cytotoxin may also be present. This cytotoxin is an ion transport ATPase which includes 87 kDa (monomer) and 972 kDa (decamer) forms. One cytotoxin is commonly termed "CagA." CagA is associated with the immunodominant antigen and is expressed on the bacterial surface. The DNA and corresponding amino acid sequences for *H. pylori* CagA are known. See, e.g., International Publication No. WO 93/18150, published 16 Sep. 1993. The native protein shows interstrain size variability due to the presence of a variable number of repeats of a 102 bp DNA segment that encodes repeats of a proline-rich amino acid sequence. See, Covacci et al., *Proc. Natl. Acad. Sci. USA* (1993) 90:5791-5795. Accordingly, the reported molecular weight of CagA ranges from about 120-135 kDa. Hence, if CagA is present in the lysate, it can be present as any of the various CagA variants, fragments thereof and muteins thereof, which retain activity.

Yet another immunogen that may be present in the lysate includes the *H. pylori* VacA protein. The DNA and corresponding amino acid sequences for *H. pylori* VacA are known and reported in, e.g., International Publication No. WO 93/18150, published 16 Sep. 1993. The gene for the VacA polypeptide encodes a precursor of about 140 kDa that is processed to an active molecule of about 90-100 kDa. This molecule, in turn, is slowly proteolytically cleaved to generate two fragments that copurify with the intact 90 kDa molecule. See, Telford et al., *Trends in Biotech*. (1994) 12:420-426. Thus, the lysate can include the precursor protein, as well as the processed active molecule, active proteolytic fragments thereof or portions or muteins thereof, which retain biological activity.

It is to be understood that the lysate can also include other immunogens not specifically described herein.

By "an *H. cerdo* lysate" is meant an extract or lysate derived from an *H. cerdo* whole bacterium which includes one or more *H. cerdo* immunogenic polypeptides. Thus, an *H. cerdo* lysate can include one or more immunogenic polypeptides corresponding to the *H. pylori* immunogens described immediately above.

The term "polypeptide" when used with reference to an *Helicobacter* immunogen, such as VacA, CagA or any of the other immunogens described above, refers to a VacA, CagA etc., whether native, recombinant or synthetic, which is derived from any *Helicobacter* strain. The polypeptide need not include the full-length amino acid sequence of the reference molecule but can include only so much of the molecule as necessary in order for the polypeptide to retain immunogenicity and/or the ability to treat or prevent *H. cerdo* infection, as described below. Thus, only one or few epitopes of the reference molecule need be present. Furthermore, the polypeptide may comprise a fusion protein between the full-length reference molecule or a fragment of the reference molecule, and another protein that does not disrupt the reactivity of the *Helicobacter* polypeptide. It is readily apparent that the polypeptide may therefore comprise the full-length sequence, fragments, truncated and partial sequences, as well as analogs and precursor forms of the reference molecule. The term also intends deletions, additions and substitutions to the reference sequence, so long as the polypeptide retains immunogenicity.

Thus, the full-length proteins and fragments thereof, as well as proteins with modifications, such as deletions, additions and substitutions (either conservative or non-conservative in nature), to the native sequence, are intended for use herein, so long as the protein maintains the desired activity. These modifications may be deliberate, as through site-directed mutagenesis, or may be accidental, such as through mutations of hosts which produce the proteins or errors due to PCR amplification. Accordingly, active proteins substantially homologous to the parent sequence, e.g., proteins with 70, 80, 85, 90, 95, 98, 99% etc. identity that retain the biological activity, are contemplated for use herein.

The term "analog" refers to biologically active derivatives of the reference molecule, or fragments of such derivatives, that retain activity, as described above. In general, the term "analog" refers to compounds having a native polypeptide sequence and structure with one or more amino acid additions, substitutions and/or deletions, relative to the native molecule. Particularly preferred analogs include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) nonpolar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 or 50 conservative or non-conservative amino acid substitutions, or any number between 5-50, so long as the desired function of the molecule remains intact.

A "purified" protein or polypeptide is a protein which is recombinantly or synthetically produced, or isolated from its natural host, such that the amount of protein present in a composition is substantially higher than that present in a crude preparation. In general, a purified protein will be at least about 50% homogeneous and more preferably at least about 80% to 90% homogeneous.

By "biologically active" is meant a Helicobacter protein that elicits an immunological response, as defined below.

By "epitope" is meant a site on an antigen to which specific B cells and T cells respond. The term is also used interchangeably with "antigenic determinant" or "antigenic determinant site." An epitope can comprise 3 or more amino acids in a spatial conformation unique to the epitope. Generally, an epitope consists of at least 5 such amino acids and, more usually, consists of at least 8-10 such amino acids. Methods of determining spatial conformation of amino acids are known in the art and include, for example, x-ray crystallography and 2-dimensional nuclear magnetic resonance. Furthermore, the identification of epitopes in a given protein is readily accomplished using techniques well known in the art, such as by the use of hydrophobicity studies and by site-directed serology. See, also, Geysen et al., *Proc. Natl. Acad. Sci. USA* (1984) 81:3998-4002 (general method of rapidly synthesizing peptides to determine the location of immunogenic epitopes in a given antigen); U.S. Pat. No. 4,708,871 (procedures for identifying and chemically synthesizing epitopes of antigens); and Geysen et al., *Molecular Immunology* (1986) 23:709-715 (technique for identifying peptides with high affinity for a given antibody). Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to the composition or vaccine of interest. Usually, an "immunological response" includes but is not limited to one or more of the following effects: the production of antibodies, B cells, helper T cells, suppressor T cells, and/or cytotoxic T cells and/or γδ T cells, directed specifically to an antigen or antigens included in the composition or vaccine of interest. Preferably, the host will display a protective immunological response to the Helicobacter immunogen(s) in question, e.g., the host will be protected from subsequent infection by *H. cerdo* and such protection will be demonstrated by either a reduction or lack of symptoms normally displayed by an infected host or a quicker recovery time.

The terms "immunogenic" protein or polypeptide refer to an amino acid sequence which elicits an immunological response as described above. An "immunogenic" protein or polypeptide, as used herein, includes the full-length sequence of the particular Helicobacter immunogen in question, including any precursor and mature forms, analogs thereof, or immunogenic fragments thereof. By "immunogenic fragment" is meant a fragment of the Helicobacter immunogen in question which includes one or more epitopes and thus elicits the immunological response described above.

Immunogenic fragments, for purposes of the present invention, will usually be at least about 2 amino acids in length, more preferably about 5 amino acids in length, and most preferably at least about 10 to 15 amino acids in length. There is no critical upper limit to the length of the fragment, which could comprise nearly the full-length of the protein sequence, or even a fusion protein comprising two or more epitopes of the Helicobacter immunogen in question.

"Homology" refers to the percent identity between two polynucleotide or two polypeptide moieties. Two DNA, or two polypeptide sequences are "substantially homologous" to each other when the sequences exhibit at least about 50% preferably at least about 75%, more preferably at least about 80%-85%, preferably at least about 90%, and most preferably at least about 95%-98% sequence identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National Biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are well known in the art.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

A "coding sequence" or a sequence that "encodes" a selected polypeptide, is a nucleic acid molecule which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

By "vector" is meant any genetic element, such as a plasmid, phage, transposon, cosmid, chromosome, virus, virion, etc., which is capable of replication when associated with the proper control elements and which can transfer gene sequences to cells. Thus, the term includes cloning and expression vehicles, as well as viral vectors.

By "recombinant vector" is meant a vector that includes a heterologous nucleic acid sequence which is capable of expression in vitro or in vivo.

The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) *Virology*, 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties into suitable host cells.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

A "nucleic acid" sequence refers to a DNA or RNA sequence. The term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxy-amino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters".

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

For the purpose of describing the relative position of nucleotide sequences in a particular nucleic acid molecule throughout the instant application, such as when a particular nucleotide sequence is described as being situated "upstream," "downstream," "3 prime (3')" or "5 prime (5')" relative to another sequence, it is to be understood that it is the position of the sequences in the "sense" or "coding" strand of a DNA molecule that is being referred to as is conventional in the art.

By "vertebrate subject" is meant any member of the subphylum chordata, including, without limitation, mammals such as cattle, sheep, pigs, goats, horses, and humans; domestic animals such as dogs and cats; and birds, including domestic, wild and game birds such as cocks and hens including chickens, turkeys and other gallinaceous birds; and fish. The term does not denote a particular age. Thus, both adult and newborn animals, as well as fetuses, are intended to be included.

The terms "effective amount" or "therapeutically effective amount" of a composition or agent, as provided herein, refer to a nontoxic but sufficient amount of the composition or agent to provide the desired "therapeutic effect," such as to elicit an immune response as described above, preferably preventing, reducing or reversing symptoms associated with the *Helicobacter* infection. This effect can be to alter a component of a disease (or disorder) toward a desired outcome or endpoint, such that a subject's disease or disorder shows improvement, often reflected by the amelioration of a sign or symptom relating to the disease or disorder. For example, a representative therapeutic effect can render the subject negative for *Helicobacter* infection when gastric mucosa is cultured for a *Helicobacter* pathogen. Similarly, biopsies indicating lowered IgG, IgM and IgA antibody production directed against the *Helicobacter* pathogen are an indication of a therapeutic effect. Similarly, decreased serum antibodies against the *Helicobacter* pathogen are indicative of a therapeutic effect. Reduced gastric inflammation is also indicative of a therapeutic effect. The exact amount required will vary from subject to subject, depending on the species, age, and general condition of the subject, the severity of the condition being treated, and the particular components of the composition administered, mode of administration, and the like. An appropriate "effective" amount in any individual case may be determined by one of ordinary skill in the art using routine experimentation.

"Treatment" or "treating" *Helicobacter* infection includes: (1) preventing the *Helicobacter* disease, or (2) causing disorders related to *Helicobacter* infection to develop or to occur at lower rates in a subject that may be exposed to *Helicobacter*, such as *H. cerdo*, (3) reducing the amount of *Helicobacter* present in a subject, and/or reducing the symptoms associated with *Helicobacter* infection.

As used herein, a "biological sample" refers to a sample of tissue or fluid isolated from an individual, including but not limited to, for example, blood, plasma, serum, fecal matter, urine, bone marrow, bile, spinal fluid, lymph fluid, samples of the skin, external secretions of the skin, respiratory, intestinal, and genitourinary tracts, samples derived from the gastric epithelium and gastric mucosa, tears, saliva, milk, blood cells, organs, biopsies and also samples of in vitro cell culture constituents including but not limited to conditioned media resulting from the growth of cells and tissues in culture medium, e.g., recombinant cells, and cell components.

As used herein, the terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof which is capable of exhibiting fluorescence in the detectable range. Particular examples of labels which may be used under the invention include fluorescein, rhodamine, dansyl, umbelliferone, Texas red, luminol, acradimum esters, NADPH and α-β-galactosidase.

MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

Central to the present invention is the discovery of a new *Helicobacter* species isolated from swine with gastritis/ulcer disease. This organism, named *H. cerdo* (Hc) by the inventors herein, produces gastric disease in young piglets that is similar to the Hp-associated active gastritis in humans. Moreover, immunogens from *H. cerdo* provide protection against subsequent challenge with *Helicobacter* species and provide diagnostic reagents for detecting *Helicobacter* infection, such as *H. cerdo* infection, in vertebrate subjects such as swine. *H. cerdo* vaccines can be used against a wide range of *Helicobacter* isolates. Moreover, the vaccines are safe, economic, have an indefinite shelf life and can be efficiently administered parenterally.

Also central to the present invention is the development of a new animal model useful for studying the pathogenesis, treatment and prevention of *Helicobacter* infection, such as *H. pylori* and *H. cerdo* infection. Gnotobiotic piglets can be used to study the ability of various *Helicobacter* vaccines, such as *H. pylori* and *H. cerdo* vaccines discussed above, to prevent *H. cerdo* infection. Additionally, gnotobiotic piglets infected with *H. cerdo* can be used to screen various compounds for their ability to treat *Helicobacter* infection caused by, e.g., *H. pylori* or *H. cerdo*.

In order to further an understanding of the invention, a more detailed discussion is provided below regarding the *Helicobacter* animal models, *H. pylori* vaccines, *Helicobacter* immunogens, as well as various uses thereof.

*Helicobacter* Animal Models

As explained above, the gnotobiotic piglet is especially suited for studying bacterial gastritis/ulcer disease caused by *H. pylori*. See, e.g., Krakowka et al. (1987) *Infect. Immun.* 55:2789-2796. Gnotobiotic swine are monogastric omnivores with gastric anatomy and physiology that closely replicates humans. Bertram et al. (1991) *Rev. Infect. Dis.* 13:S714-S722. These pigs are susceptible to oral colonization with many different *H. pylori* strains. Krakowka et al. (1987) *Infect. Immun.* 55:2789-2796; Bertram et al. (1991) *Rev. Infect. Dis.* 13:S714-S722. The inventors herein have discovered that this animal model is also suited for studying the newly identified porcine *Helicobacter* pathogen, *H. cerdo*, and therefore for identifying vaccine candidates, such as *H. pylori* vaccines (i.e., vaccines including one or more immunogens derived from *H. pylori*) and *H. cerdo* vaccines (i.e., vaccines including one or more immunogens derived from *H. cerdo*), useful for preventing *Helicobacter* infection in pigs. Thus, a preferred use for the animal models of the invention is the development of vaccines for use in the prevention and/or treatment of *Helicobacter* infection in pigs and diseases associated therewith.

In this context, pigs are administered the vaccine candidate at least once, and preferably boosted with at least one additional immunization. For example, gnotobiotic piglets can be administered a vaccine composition to be tested at 1-5 days of age, followed by a subsequent boost 5-10 days later, and optionally a third immunization 5-10 days following the second administration. Piglets can be vaccinated as many times as necessary. The vaccinated piglets are then exposed to *H. cerdo* approximately 3-20 days later, such as 4-10 days following the last immunization. Typically, vaccinated piglets are orally administered from about $10^6$-$10^{10}$, more particularly about $10^7$-$10^9$, such as about $10^8$-$10^9$ colony forming units (cfu) of *H. cerdo*, and indicia of *Helicobacter* infection are monitored, such as described in the examples herein. For example, the establishment of *H. cerdo* infection can be confirmed by examining tissue samples for bacteria and/or signs of inflammation, ulceration or carcinoma.

Alternatively, gnotobiotic piglets can first be infected with *H. cerdo* bacteria in order to establish *Helicobacter* infection.

For example, piglets can be orally inoculated at 1-5 days of age with *H. cerdo*, in an amount sufficient to cause infection, such as with about $10^6$-$10^{10}$, more particularly about $10^7$-$10^9$, such as about $10^8$, cfu of *H. cerdo*. The presence of *H. cerdo* infection can be confirmed by examining tissue samples for bacteria and/or signs of inflammation, ulceration or carcinoma. In alternative embodiments, *H. cerdo*-inoculated pigs can be fed a milk-replacement diet that contains a dietary source of fermentable carbohydrate in order to cause gastroesophageal ulceration (GEU) of the pars esophagea. In this embodiment, pigs are typically fed a replacement formula well known in the art, such as but not limited to SIMILAC or ESBILAC, supplemented with a source of fermentable carbohydrate, such as but not limited to corn syrup, cornstarch, inulin, lactulose, wheat starch, sugar beet pulp, raffinose, stachyose, any of several oligosaccharides such as fructooligosaccharides, transgalactooligosaccharides, glucooligosaccharides, mannanoligosaccharides, xylooligosaccharides, or combinations of the above. Carbohydrate supplementation is typically introduced gradually, for example about 2-7% (v/v), preferably about 3-6% (v/v), such as about 5% (v/v), beginning 1-10 days after *H. cerdo* inoculation, such as beginning at 3-8 days, preferably 2-4 days after *H. cerdo* inoculation. The amount of carbohydrate can be increased to, e.g., about 8-15% (v/v), typically about 9-12% (v/v), such as about 10% (v/v), when the piglets accommodate to the additive, typically after 3-14 days following initial supplementation, generally 5-10 days following initial supplementation.

Once the bacterial infection has been established and, if desired, the milk-replacement diet described above is administered, a compound or a series of compounds can be delivered to the infected piglet at various times and in various dosages, depending on the particular goals of the screen. In a variation of this procedure, it may be desirable to administer the bacteria with a compound to determine whether, relative to control animals, the compound can effectively prevent in vivo the initial bacterial adhesion and/or the subsequent establishment of infection or pathogenesis.

Thus, the infected piglets can be used to screen for compounds and conditions which prevent *Helicobacter* infection, such as compounds and conditions that block binding of *Helicobacter* pathogens to the gut epithelium and/or that ameliorate the *Helicobacter*-associated pathogenesis of gastritis and gastric adenocarcinoma. The efficacy of the compound or compounds can be assessed by examining at selected times the cells of the gut epithelial tissue of the infected animals for the presence or loss of *Helicobacter* bacteria and/or the development, inhibition, or amelioration of ulcer or tumor formation relative to appropriate control animals, for example, untreated *H. cerdo*-infected animals. The animal models described herein therefore provide the ability to readily assess the efficacy of various drugs or compounds based on different modes of administration and compound formation.

In addition to using the *H. cerdo*-infected animals to screen for therapeutic compounds, these animals can also be used to screen for conditions or stimuli which effect a block in or ameliorate *Helicobacter*, infection and/or associated gut diseases. Such stimuli or conditions include environmental or dietary changes, changing the gastrointestinal pH, or combinations of various stimuli or conditions which result in stress on the animal or on *Helicobacter* bacteria in the gut. Thus, *H. cerdo*-infected animals can be exposed to a selected stimulus or condition, or a combination of stimuli or conditions, to be tested. The gut epithelial tissue of exposed animals is then examined periodically for a change in the number of *Helicobacter* bacteria and/or the disease state of the epithelial tissue relative to non-exposed control animals.

Another type of condition that can be tested for in the *H. cerdo*-inoculated animals described herein is the induction of an inflammatory response, for example by administering a chemical agent such as dextran sulfate, at various times prior to, during, or after administration of *H. cerdo* to the gnotobiotic piglet. The inflammatory agent can be administered orally or by any other mode that results in a gastrointestinal inflammatory response. The severity of the inflammatory response can be controlled by varying the dose and the duration of treatment with the chemical agent.

*Helicobacter* Vaccines

As explained above, the animal models described herein can be used to identify *Helicobacter* vaccines, such as *H. pylori* vaccines, useful for preventing *Helicobacter* infection in swine such as caused by *H. cerdo*. *Helicobacter* vaccines useful for treating *H. cerdo* infection can take various forms, such as inactivated or attenuated *Helicobacter* vaccines, including vaccines with antigenically enhanced bacteria, such as the *H. pylori* vaccine described in e.g., U.S. Pat. No. 5,897,475, incorporated herein by reference in its entirety, as well as subunit vaccines that contain one or more *Helicobacter* immunogens, such as vaccines that include urease or urease subunits and/or epitopes, such as the *H. pylori* vaccines described in U.S. Pat. Nos. 5,972,336 and 6,290,962 incorporated herein by reference in their entireties. Other useful *Helicobacter* vaccines include those that comprise the catalase enzyme or immunogenic fragments thereof, such as the *H. pylori* vaccines described in U.S. Pat. Nos. 6,005,090 and 6,468,545, incorporated herein by reference in their entireties; as well as the whole cell immunogens described in e.g., U.S. Pat. No. 6,841,155, incorporated herein by reference in its entirety.

As explained above, several other *Helicobacter* immunogens exist and will find use in *Helicobacter* vaccines, such as *H. pylori* vaccines for preventing *H. cerdo* infection. Such immunogens include VacA including the precursor protein, as well as the processed active molecule, active proteolytic fragments thereof or portions or muteins thereof, which retain immunogenic activity; either or both of FlaA and FlaB; the UreA and UreB subunits of the urease holoenzyme, as well as the urease holoenzyme and epitopes therefrom; CagA in any of its various forms as described above; any of the *Helicobacter* adhesins such as, but not limited to, the 20 kDa N-acetyl-neuraminillactose-binding fibrillar haemagglutinin (HpaA), and the 63 kDa protein that binds phosphatidylethanolamine and gangliotetraosyl ceramide, and a conserved fimbrial pilus-like structure; hsp60; neutrophil activating protein (NAP), see, e.g., Evans et al. (1995) *Gene* 153:123-127; and PCT Publication Nos. WO 96/01272 and WO 96/01273; the antigens known as HopX, HopY, 36 kDa, 42 kDa, and 17 kDa antigens (see PCT Publication No. WO 98/04702) and the 50 kDa antigen (see European Publication No. EP 0793676).

The immunogens for use in vaccine compositions can be produced using a variety of techniques. For example, the immunogens can be obtained directly from *Helicobacter* bacteria, commercially available from, e.g., the American Type Culture Collection (ATCC), 10801 University Boulevard, Manassas, Va. The *Helicobacter* immunogens from the bacteria can be provided in a lysate, obtained using methods well known in the art. Generally, such methods entail extracting proteins from *Helicobacter* bacteria using such techniques as sonication or ultrasonication; agitation; liquid or solid extrusion; heat treatment; freeze-thaw techniques; explosive decompression; osmotic shock; proteolytic digestion such as treatment with lytic enzymes including proteases such as pepsin, trypsin, neuraminidase and lysozyme; alkali treatment; pressure disintegration; the use of detergents and solvents such as bile salts, sodium dodecylsulphate, TRITON (an octylphenol ethoxylate), NP40 and CHAPS; fractionation, and the like. The particular technique used to disrupt the cells is largely a matter of choice and will depend on the culture conditions and any pre-treatment used. Following disruption of the cells, cellular debris can be removed, generally by centrifugation and/or dialysis.

One particular technique for obtaining an *H. pylori* lysate vaccine composition is described in the examples herein and uses proteolytic digestion, according to a method similar to the digestion protocol described in Waters et al. (2000) *Vaccine* 18:711-719. In this technique, *H. pylori* bacteria are recovered by centrifugation and the bacterial pellet is resuspended, frozen and lyophilized. For bacterial digestion, pepsin is incubated with the lyophilized bacteria for 24-30 hours at 37 degrees C.

The immunogens present in such lysates can be further purified if desired, using standard purification techniques such as but not limited to, column chromatography, ion-exchange chromatography, size-exclusion chromatography, electrophoresis, HPLC, immunoadsorbent techniques, affinity chromatography, immunoprecipitation, and the like. See, e.g., PCT Publication No. WO 96/12965, published 2 May 1996, for a description of the purification of several antigens from *H. pylori*.

The *Helicobacter* immunogens can also be generated using recombinant methods, well known in the art. In this regard, oligonucleotide probes can be devised based on the sequence of the particular *Helicobacter* genome and used to probe genomic or cDNA libraries for *Helicobacter* genes encoding for the antigens useful in the present invention. The genes can then be further isolated using standard techniques and, if desired, restriction enzymes employed to mutate the gene at desired portions of the full-length sequence.

Similarly, *Helicobacter* genes can be isolated directly from bacterial cells using known techniques, such as phenol extraction, and the sequence can be further manipulated to produce any desired alterations. See, e.g., Sambrook et al., supra, for a description of techniques used to obtain and isolate DNA. Finally, the genes encoding the *Helicobacter* immunogens can be produced synthetically, based on the known sequences. The nucleotide sequence can be designed with the appropriate codons for the particular amino acid sequence desired. In general, one will select preferred codons for the intended host in which the sequence will be expressed. The complete sequence is generally assembled from overlapping oligonucleotides prepared by standard methods and assembled into a complete coding sequence. See, e.g., Edge, *Nature* (1981) 292:756; Nambair et al., *Science* (1984) 223:1299; Jay et al., *J. Biol. Chem.* (1984) 259:6311.

Once coding sequences for the desired polypeptides have been isolated or synthesized, they can be cloned into any suitable vector or replicon for expression in a variety of systems, including insect, mammalian, bacterial, viral and yeast expression systems, all well known in the art. In particular, host cells are transformed with expression vectors which include control sequences operably linked to the desired coding sequence. The control sequences will be compatible with the particular host cell used. It is often desirable that the polypeptides prepared using the above systems be fusion polypeptides. As with nonfusion proteins, these proteins may be expressed intracellularly or may be secreted from the cell into the growth medium.

Furthermore, plasmids can be constructed which include a chimeric gene sequence, encoding e.g., multiple *Helicobacter* antigens. The gene sequences can be present in a dicistronic gene configuration. Additional control elements can be situated between the various genes for efficient translation of RNA from the distal coding region. Alternatively, a chimeric transcription unit having a single open reading frame encoding the multiple antigens can also be constructed. Either a fusion can be made to allow for the synthesis of a chimeric protein or alternatively, protein processing signals can be engineered to provide cleavage by a protease such as a signal peptidase, thus allowing liberation of the two or more proteins derived from translation of the template RNA. The processing protease may also be expressed in this system either independently or as part of a chimera with the antigen and/or cytokine coding region(s). The protease itself can be both a processing enzyme and a vaccine antigen.

Depending on the expression system and host selected, the immunogens of the present invention are produced by growing host cells transformed by an expression vector under conditions whereby the immunogen of interest is expressed. The immunogen is then isolated from the host cells and purified. If the expression system provides for secretion of the immunogen, the immunogen can be purified directly from the media. If the immunogen is not secreted, it is isolated from cell lysates. The selection of the appropriate growth conditions and recovery methods are within the skill of the art.

The *Helicobacter* immunogens may also be produced by chemical synthesis such as by solid phase or solution peptide synthesis, using methods known to those skilled in the art. Chemical synthesis of peptides may be preferable if the antigen in question is relatively small. See, e.g., J. M. Stewart and J. D. Young, *Solid Phase Peptide Synthesis*, 2nd Ed., Pierce Chemical Co., Rockford, Ill. (1984) and G. Barany and R. B. Merrifield, *The Peptides: Analysis, Synthesis, Biology*, editors E. Gross and J. Meienhofer, Vol. 2, Academic Press, New York, (1980), pp. 3-254, for solid phase peptide synthesis techniques; and M. Bodansky, *Principles of Peptide Synthesis*, Springer-Verlag, Berlin (1984) and E. Gross and J. Meienhofer, Eds., *The Peptides: Analysis, Synthesis, Biology*, supra, Vol. 1, for classical solution synthesis.

Formulations and Administration

The *Helicobacter* immunogens, such as *H. pylori* lysates, can be formulated into compositions, such as vaccine compositions, either alone or in combination with other antigens, for use in immunizing porcine subjects as described below. Methods of preparing such formulations are described in, e.g., *Remington's Pharmaceutical Sciences*, Mack Publishing Company, Easton, Pa., 18 Edition, 1990. Typically, the vaccines of the present invention are prepared as injectables, either as liquid solutions or suspensions. Solid forms suitable for solution in or suspension in liquid vehicles prior to injection may also be prepared. The preparation may also be emulsified or the active ingredient encapsulated in liposome vehicles. The active immunogenic ingredient is generally mixed with a compatible pharmaceutical vehicle, such as, for example, water, saline, dextrose, glycerol, ethanol, or the like, and combinations thereof. In addition, if desired, the vehicle may contain minor amounts of auxiliary substances such as wetting or emulsifying agents and pH buffering agents.

Adjuvants which enhance the effectiveness of the vaccine may also be added to the formulation. Adjuvants may include for example, muramyl dipeptides, avridine, aluminum hydroxide, alum, Freund's adjuvant, incomplete Freund's adjuvant (ICFA), dimethyldioctadecyl ammonium bromide (DDA), oils, oil-in-water emulsions, saponins, cytokines, and other substances known in the art. Such adjuvants are well known and commercially available from a number of sources, e.g., Difco, Pfizer Animal Health, Newport Laboratories, etc.

The immunogens may also be linked to a carrier in order to increase the immunogenicity thereof. Suitable carriers include large, slowly metabolized macromolecules such as proteins, including serum albumins, keyhole limpet hemocyanin, immunoglobulin molecules, thyroglobulin, ovalbumin, and other proteins well known to those skilled in the art; polysaccharides, such as sepharose, agarose, cellulose, cellulose beads and the like; polymeric amino acids such as polyglutamic acid, polylysine, and the like; amino acid copolymers; and inactive virus particles.

The immunogens may be used in their native form or their functional group content may be modified by, for example, succinylation of lysine residues or reaction with Cys-thiolactone. A sulfhydryl group may also be incorporated into the carrier (or antigen) by, for example, reaction of amino functions with 2-iminothiolane or the N-hydroxysuccinimide ester of 3-(4-dithiopyridyl propionate. Suitable carriers may also be modified to incorporate spacer arms (such as hexamethylene diamine or other bifunctional molecules of similar size) for attachment of peptides.

Furthermore, the immunogens may be formulated into vaccine compositions in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Vaccine formulations will contain a "therapeutically effective amount" of the active ingredient, that is, an amount capable of eliciting an immune response in a subject to which the composition is administered. In the treatment and prevention of *Helicobacter* infection in pigs, a "therapeutically effective amount" is readily determined by one skilled in the art using standard tests. The *Helicobacter* immunogens will typically range from about 1% to about 95% (w/w) of the composition, or even higher or lower if appropriate. With the present vaccine formulations, about 0.1 to about 500 mg of active ingredient per ml, preferably about 1 to about 100 mg/ml, more preferably about 10 to about 50 mg/ml, such as about 20, 25, 30, 35, 40, etc., or any number within these stated ranges, of injected solution should be adequate to raise an immunological response when a dose of about 0.25 to 3 ml per animal is administered.

To immunize a subject, the vaccine is generally administered parenterally, usually by intramuscular injection. Other modes of administration, however, such as subcutaneous, intraperitoneal and intravenous injection, are also acceptable. The quantity to be administered depends on the animal to be treated, the capacity of the animal's immune system to synthesize antibodies, and the degree of protection desired. Effective dosages can be readily established by one of ordinary skill in the art through routine trials establishing dose response curves. The subject is immunized by administration of the vaccine in at least one dose, and preferably two or more doses. Moreover, the animal may be administered as many doses as is required to maintain a state of immunity to infection.

Additional vaccine formulations which are suitable for other modes of administration include suppositories and, in some cases, aerosol, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about 10% to about 95% of the active ingredient, preferably about 25% to about 70%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Controlled or sustained release formulations are made by incorporating the protein into carriers or vehicles such as liposomes, nonresorbable impermeable polymers such as ethylenevinyl acetate copolymers and Hytrel copolymers, swellable polymers such as hydrogels, or resorbable polymers such as collagen and certain polyacids or polyesters such as those used to make resorbable sutures. The *Helicobacter* immunogens can also be delivered using implanted mini-pumps, well known in the art.

The *Helicobacter* immunogens can also be administered via a carrier virus which expresses the same. Carrier viruses which will find use with the instant invention include but are not limited to the vaccinia and other pox viruses, adenovirus, and herpes virus. By way of example, vaccinia virus recombinants expressing the novel proteins can be constructed as follows. The DNA encoding the particular protein is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the instant protein into the viral genome. The resulting $TK^-$ recombinant can be selected by culturing the cells in the presence of 5-bromodeoxyuridine and picking viral plaques resistant thereto.

An alternative route of administration involves gene therapy or nucleic acid immunization. Thus, nucleotide sequences (and accompanying regulatory elements) encoding the *Helicobacter* immunogens can be administered directly to a subject for in vivo translation thereof. Alternatively, gene transfer can be accomplished by transfecting the subject's cells or tissues ex vivo and reintroducing the transformed material into the host. DNA can be directly introduced into the host organism, i.e., by injection (see International Publication No. WO/90/11092; and Wolff et al. (1990) *Science* 247:1465-1468). Liposome-mediated gene transfer can also be accomplished using known methods. See, e.g., Hazinski et al. (1991) *Am. J. Respir. Cell Mol. Biol.* 4:206-209; Brigham et al. (1989) *Am. J. Med. Sci.* 298:278-281; Canonico et al. (1991) *Clin. Res.* 39:219A; and Nabel et al. (1990) *Science* 1990) 249:1285-1288. Targeting agents, such as antibodies directed against surface antigens expressed on specific cell types, can be covalently conjugated to the liposomal surface so that the nucleic acid can be delivered to specific tissues and cells susceptible to infection.

The compositions of the present invention can be administered prior to, subsequent to or concurrently with traditional antimicrobial agents used to treat *Helicobacter* disease, such as but not limited to bismuth subsalicylate, metronidazole, amoxicillin, omeprazole, clarithromycin, ciprofloxacin, erythromycin, tetracycline, nitrofurantoin, ranitidine, omeprazole, and the like. One particularly preferred method of treatment is to first administer conventional antibiotics as described above followed by vaccination with the compositions of the present invention once the *Helicobacter* infection has cleared.

Diagnostics

The *H. cerdo* immunogens, including *H. cerdo* lysates, can also be used as diagnostics to detect the presence of reactive antibodies directed against the bacterium in a biological sample. Furthermore, the immunogens can be used to monitor the course of antibiotic therapy by comparing results obtained at the outset of therapy to those obtained during and after a course of treatment. For example, the presence of antibodies reactive with the *H. cerdo* antigens can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, enzymatic labels or dye molecules, or other methods for detecting the formation of a complex between the antigen and the antibody or antibodies reacted therewith.

The aforementioned assays generally involve separation of unbound antibody in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g, beads or microtiter plates); polyvinylidine fluoride; diazotized paper; nylon membranes; activated beads, magnetically responsive beads, and the like.

Typically, a solid support is first reacted with a solid phase component (e.g., one or more *H. cerdo* antigens, such as an *H. cerdo* lysate produced by proteolytic digestion of *H. cerdo* bacteria) under suitable binding conditions such that the component is sufficiently immobilized to the support. Sometimes, immobilization of the antigen to the support can be enhanced by first coupling the antigen to a protein with better binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those of skill in the art. Other molecules that can be used to bind the antigens to the support include polysaccharides, polylactic acids, polyglycolic acids, polymeric amino acids, amino acid copolymers, and the like. Such molecules and methods of coupling these molecules to the antigens, are well known to those of ordinary skill in the art. See, e.g., Brinkley, M. A., *Bioconjugate Chem*. (1992) 3:2-13; Hashida et al., *J. Appl. Biochem*. (1984) 6:56-63; and Anjaneyulu and Staros, *International J. of Peptide and Protein Res*. (1987) 30:117-124.

After reacting the solid support with the solid phase component, any non-immobilized solid-phase components are removed from the support by washing, and the support-bound component is then contacted with a biological sample suspected of containing ligand moieties (e.g., antibodies toward the immobilized antigens) under suitable binding conditions. After washing to remove any non-bound ligand, a secondary binder moiety is added under suitable binding conditions, where the secondary binder is capable of associating selectively with the bound ligand. The presence of the secondary binder can then be detected using techniques well known in the art.

More particularly, an ELISA method can be used, where the wells of a microtiter plate are coated with the *H. cerdo* antigen(s). A biological sample containing or suspected of containing anti-*H. cerdo* immunoglobulin molecules is then added to the coated wells. In assays where it is desired to use one microtiter plate, a selected number of wells can be coated with, e.g., a first antigen moiety, a different set of wells coated with a second antigen moiety, and so on. In the alternative, a series of ELISAs can be run in tandem. After a period of incubation sufficient to allow antibody binding to the immobilized antigens, the plate(s) can be washed to remove unbound moieties and a detectably labeled secondary binding molecule added. The secondary binding molecule is allowed to react with any captured sample antibodies, the plate washed and the presence of the secondary binding molecule detected using methods well known in the art.

Thus, in one particular embodiment, the presence of bound anti-*H. cerdo* antigen ligands from a biological sample can be readily detected using a secondary binder comprising an antibody directed against the antibody ligands. A number useful immunoglobulin (Ig) molecules are known in the art and commercially available. Ig molecules for use herein will preferably be of the IgG or IgA type, however, IgM may also be appropriate in some instances. The Ig molecules can be readily conjugated to a detectable enzyme label, such as horseradish peroxidase, glucose oxidase, Beta-galactosidase, alkaline phosphatase and urease, among others, using methods known to those of skill in the art. An appropriate enzyme substrate is then used to generate a detectable signal. In other related embodiments, competitive-type ELISA techniques can be practiced using methods known to those skilled in the art.

Assays can also be conducted in solution, such that the bacterial proteins and antibodies specific for those bacterial proteins form complexes under precipitating conditions. In one particular embodiment, the *H. cerdo* antigen(s) can be attached to a solid phase particle (e.g., an agarose bead or the like) using coupling techniques known in the art, such as by direct chemical or indirect coupling. The antigen-coated particle is then contacted under suitable binding conditions with a biological sample suspected of containing antibodies for *H. cerdo*. Cross-linking between bound antibodies causes the formation of particle-antigen-antibody complex aggregates which can be precipitated and separated from the sample using washing and/or centrifugation. The reaction mixture can be analyzed to determine the presence or absence of antibody-antigen complexes using any of a number of standard methods, such as those immunodiagnostic methods described above.

In yet a further embodiment, an immunoaffinity matrix can be provided, wherein a polyclonal population of antibodies from a biological sample suspected of containing anti-*H. cerdo* antibodies is immobilized to a substrate. In this regard, an initial affinity purification of the sample can be carried out using immobilized antigens. The resultant sample preparation will thus only contain anti-*H. cerdo* moieties, avoiding potential nonspecific binding properties in the affinity support. A number of methods of immobilizing immunoglobulins (either intact or in specific fragments) at high yield and having good retention of antigen binding activity, are known in the art. Not being limited by any particular method, immobilized protein A or protein G can be used to immobilize immunoglobulins.

Accordingly, once the immunoglobulin molecules have been immobilized to provide an immunoaffinity matrix, the *H. cerdo* antigens, having separate and distinct labels, are contacted with the bound antibodies under suitable binding conditions. After any non-specifically bound antigen has been washed from the immunoaffinity support, the presence of bound antigen can be determined by assaying for each specific label using methods known in the art.

The above-described assay reagents, including the *H. cerdo* immonogens (such as an *H. cerdo* lysate), optionally immobilized on a solid support, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

EXAMPLES

Below are examples of specific embodiments for carrying out the present invention. The examples are offered for illustrative purposes only, and are not intended to limit the scope of the present invention in any way.

Example 1

Isolation of *H. cerdo* from Porcine Gastric Mucosa

Bacteria were recovered from porcine gastric mucosa under microaerophilic conditions as follows. Stomachs were removed from young swine and opened by incision along the greater and lesser curvatures. Contents were removed and the mucosa was rinsed with sterile saline washes. Mucosal strips from the glandular cardia of the lesser curvature and mucosal antrum, 5×20 mm, (less the muscularis), were removed by sterile dissection and suspended in 5 ml of Brucella broth (Difco) supplemented with 10% fetal bovine serum (B-FBS) and the strip was placed in sterile 7.0 ml glass ten Broeck tissue grinders. The tissues were ground 10 times and 10-fold serial dilutions ($10^{-0}$ to $10^{-4}$) were made in B-FBS. $\frac{1}{10}$ ml of each dilution was plated onto agar plates containing either Skirrow's medium or TSAII (tyypticase soy agar with 5% sheep blood). Plates were incubated in a humid microaerobic environment for 3-4 days. Suspect *Helicobacter* species colonies (small pinpoint translucent and non-hemolytic) were identified and sub-passed onto fresh agar plates as above.

Aliquots of each suspect isolate were stained by the Gram's stain method and tested for urease activity (placement of a cotton swab containing the organisms into B-FBS containing urea and pH indicator) and into a solution of 1% (v/v) hydrogen peroxide in sterile distilled water. Microbes which were Gram negative short curved rods which were urease- and catalase-positive were considered to be *Helicobacter* species.

On the basis of location (stomach), morphology (Gram negative, short, curved "gull-wing-like" rods), urease activity and cross-reactivity with an anti-Hp reagent, the bacterium isolated was assigned to the genus *Helicobacter* and named *H. cerdo* (Spanish for "pork").

*H. cerdo* is distinct from, but antigenically related to Hp, and the larger spiral organism, Candidatus *Helicobacter suis* (Degroote et al. (2000) *J. Clin. Microbiol.* 38:1131-1135), another *Helicobacter* species that is found in normal swine and swine with gastritits and is therefore thought to be a nonpathogenic commensal organism.

Example 2

Infection and Recovery of *H. cerdo* from Experimentally Infected Swine

Three gnotobiotic piglets were orally infected with *H. cerdo* at three days of age and terminated at 35 days of age. A procedure similar to that detailed above was used to recover gastric bacteria from the experimentally infected swine. For this, one-half of the stomach was sterilely removed and placed into sterile pre-weighed 100 mm³ petri dishes. 5 ml of B-FBS was added and the mucosa was separated from the gastric muscularis by blunt dissection and scraping with sterile instruments. The muscularis was removed and the petri plates containing the recovered mucosa were weighed again. The mucosa and B-FBS were removed and placed into sterile 7.0 ml glass ten Broeck tissue grinders and ground as above. 10-fold serial dilutions of the homogenate were made in B-FBS and $\frac{1}{10}$ ml of each dilution was plated in duplicate onto TSAII or blood agar plates. Plates were incubated in a humid microaerobic environment for 3-4 days.

Suspect *Helicobacter* species colonies (small pinpoint translucent and non-hemolytic) were identified on each plate dilution. Discrete colonies were counted on the plate/dilution containing between 30 and 300 bacterial colonies. To determine bacterial colony forming units (cfu) per gram of gastric mucosa, the number of colonies counted between the two dilutions was averaged (total colonies counted divided by 2) and multiplied by the dilution factor ($10^{-0}$ to $10^{-4}$), by 5 (for the initial dilution in B-FBS), times 10 (for the initial dilution) to arrive at the total cfu recovered. The total cfu was divided by the weight of gastric mucosa and the resultant number was the bacterial cfu/gram of gastric mucosa.

Tables 1-4 summarize the gross observations (Table 1), histopathologic changes (Table 2), extra-gastric histopathologic findings (Table 3) and microbiologic findings (Table 4) in the infected pigs. All of the tested pigs (3/3) were culture and W/S positive in the stomach. 3/3 pigs displayed gastroesophageal ulceration (GEU) in nonglandular cardia; 2/3 showed healed antral microulcers; and 3/3 displayed lyphofollicular antral gastritis. Thus, *H. cerdo* colonized the gastric mucosa of the swine. Additionally, *H. cerdo* infection was strongly associated with gastric and duodenal ulcer disease and produced a persistent gastric bacterial infection of swine analogous to *H. pylori* in humans.

TABLE 1

A summary of gross observations in gnotobiotic piglets infected with *H. cerdo* and terminated at 35 days of age.

| Group/ Piglet No. | Wt. (g) | Sex | Excess Mucus | Lymphoid Follicles | Submucosal Edema | Skin Tests[a] 24 hr. | Skin Tests[a] 48 hr. | Ulcers and/or Erosions |
|---|---|---|---|---|---|---|---|---|
| 02-2662 | 2650 | M | 1[b] | 2 | 2 | −[c] | slight | GEU, red, lesser curvature |
| 02-2663 | 2700 | F | 2 | 2 | 0 | − | − | GEU, lesser curvature, possible ulcer in fundus |
| 02-2664 | 2960 | F | 2 | 3 | 3 | − | − | GEU, lesser curvature, possible ulcer in antrum |

[a]Skin test antigen consisted of *Helicobacter pylori* preparation, (10.0 ug 26695 clarified sonicate in 0.1 ml PBS).
[b]Visually scored as 0 = no change from normal; 1 = minimal change; 2 = moderate change; and 3 = severe change
[c]Skin test responses scored as negative (−) or positive (+) with further description.

TABLE 2

A summary of histopathologic changes in the stomachs of gnotobiotic piglets infected with *H. cerdo* and terminated at 35 days of age.

| | Anatomical Region of the Stomach | | | | | | | |
|---|---|---|---|---|---|---|---|---|
| Group/ | Cardia | | Fundus | | Antrum | | Pylorus | |
| Piglet No. | H/E | W/S[a] | H/E | W/S | H/E | W/S | H/E | W/S |
| 02-662 | 3[b] | +[c] GEU[e] | 1 | X[d] | 2 | X possible healed micro-ulcer | 0 | X |
| 02-663 | 1 | X | 1 | X | 3 | +/− | 0 | X |
| 02-664 | 3 | + | 0 | X | 3 | X possible healed micro-ulcer | 0 | X |

[a]H/E = hematoxylin and eosin stain; W/S = Warthin-Starry stain
[b]Subjectively scored as 0 = no change from normal (no inflammation); 1 = minimal change from normal; 2 = moderate change from normal; and 3 = severe change from normal.
[c]Scored as (+) for small curved extracellular micro-organisms present on the gastric luminal surface of the sections or (−): no microbes seen.
[d]X - The W/S stains are of poor quality and must be repeated before a determination of the presence of organisms can be determined.
[e]GEU: gastroesophageal ulceration in the nonglandular cardia and adjacent glandular mucosa of the lesser curvature of the stomach.

TABLE 3

A summary of extra-gastric histopathologic findings in gnotobiotic piglets infected with *H. cerdo* and terminated at 35 days of age.

| | Anatomical Region of the Stomach | | | | | | Skin test Sites (ear) | |
|---|---|---|---|---|---|---|---|---|
| Group/ Piglet No. | Esophagus | Duodenum | Jejunum | Ileum | Colon | Gastric Lymph Nodes | 24 hr. | 48 hr. |
| 02-662 | 0[a] | 0 | 0 | reactive Peyer's patches | 0 | reactive hyperplasia | 0[b] mononuclear cell infiltrates | 1 |
| 02-663 | 0 | villous atrophy | 0 | reactive Peyer's patches | 0 | nd[c] PMNs & mononuclears | 1 | 0 |
| 02-664 | 0 | 0 | 0 | reactive Peyer's patches | reactive follicles | reactive lymphoid hyperplasia | 0 mononuclear cell infiltrates | 1 |

[a]Subjectively scored as 0 = no change from normal (no inflammation); 1 = minimal change from normal; 2 = moderate change from normal; and 3 = severe change from normal on H/E-stained sections.
[b]Skin test sites (ear) scored as 0 (no inflammatory cell infiltrate) or 1 (modest inflammatory cell infiltrates
[c]nd: not done

TABLE 4

A summary of microbiologic findings in gnotobiotic piglets infected with *H. cerdo* and terminated at 35 days of age.

| Group/ Piglet No. | H. cerdo at Termination (PID 35) | | | | Other Microbial Contaminants |
|---|---|---|---|---|---|
| | cfu/gm | Urease | Cata | Oxi | |
| 02-2662 | $5.54 \times 10^5$ | + | + | + | none |
| 02-2663 | + (re-streaks) | + | + | + | none |
| 02-2664 | $5.52 \times 10^6$ | + | + | + | none |

Example 3

Prevention of *H. cerdo* Infection Using an *H. cerdo* Lysate

An *H. cerdo* vaccine was prepared using proteolytic digestion to produce an *H. cerdo* lysate, according to a method similar to the digestion protocol described in Waters et al. (2000) *Vaccine* 18:711-719. In particular, suspensions of *H. cerdo* bacteria propagated in liquid cultures of B-FBS under microaerophilic conditions were allowed to reach approximately $10^9$ bacteria per ml. The bacteria were recovered by centrifugation (2000-3000×g) for 10 minutes. The spent supernatant was discarded and the bacterial pellet was resuspended in a minimal amount of Dulbecco's phosphate-buffered saline, transferred to a plastic cryo vial and frozen at −70 degrees C. While frozen, the bacterial pellet was lyophilized in a centrifugal evaporator apparatus (speed vac). Lyophilized bacterial pellets were pooled and weighed. For bacterial digestion, pepsin (Sigma, St. Louis, Mo.) at a concentration of 1.0 µg/ml was prepared by dilution into 10 mM HCl, pH 1.9-2.2. 1 µg of pepsin was incubated with 1 mg of lyophilized bacteria for 24-25 hours at 37 degrees C. on a magnetic stirrer. After completion of digestion, the digest was aliquoted, labeled and frozen at −70 degrees C. until use.

The *H. cerdo* lysate was formulated into a vaccine composition and used to vaccinate gnotobiotic pigs as follows. The lysate was diluted to 24-25 mg/ml in Dulbecco's phosphate-buffered saline and mixed with 1 ml of adjuvant. The vaccine was emulsified in adjuvant and 0.5 ml of the mixture was injected into the dorsal axillas and hips of each piglet. Each piglet received 3 injections at 3, 10 and 17 days of age. (See Table 5.)

The results indicated significant reduction in pathogen loads and disease sparing in vaccinated pigs, demonstrating the efficacy of this immunoprophylactic approach. In particular, as seen in the tables herein, *H. cerdo* infects piglets and persistently colonizes gastric mucosa and segments of the proximal small intestine. *H. cerdo* is associated with gastric ulcer disease. Homologous, parenterally administered vaccine protected against subsequent oral challenge with infection by *H. cerdo*. (See Table 6.)

TABLE 5

Experimental Design and Evaluation

| Group/Piglet No. | Vaccinate at 3, 10 and 17 days of age with: | | Infect with H. cerdo on day 21: |
|---|---|---|---|
| | H. pylori digest | H. cerdo digest | 24 days of age |
| Isolator no. 1 | | | |
| A (n = 2) | yes | — | yes |
| B (n = 2) | — | yes | yes |
| C (n = 2) | — | — | yes |

1. Piglets were terminated approximately 2 weeks after challenge with *H. cerdo* (35 days of age).

2. One-half of the stomach was removed, weighed, mucosa scraped free of the muscularis and weighed again. A 10% (w/v) homogenate was made and quantitative re-isolation of organisms was determined by titration onto microtiter plates. Organisms were confirmed to be of *Helicobacter* sp by urease, catalase assays, Gram's stain and colony morphology.

3. The remaining one-half stomach was examined for histologic evidence of disease by standard methods.

4. For the two piglets of group C, sterile samples of esophagus, duodenum, jejenum, ileum, spiral colon, descending colon and terminal colon was also cultured for the presence of organisms (positive or negative, nonquantitative), to determine if *H. suis* is a stomach-specific pathogen of swine as *H. pylori* is in experimentally infected gnotobiotic swine and also in humans.

TABLE 6

A summary of gross observations in gnotobiotic piglets vaccinated with protease digests, infected with *H. cerdo* and terminated at 35 days of age.

| Group/ Piglet No. | Wt. (g) | Sex | Excess Mucus | Lymphoid Follicles | Submucosal Edema | Ulcers and/or Erosions |
|---|---|---|---|---|---|---|
| Vaccinated with *H. pylori* digest and infected with *H. cerdo* | | | | | | |
| 02-3481 | 2750 | F | $0^a$ | +/− | 0 | none |
| 02-3482 | 3400 | M | 1 | 0 | 0 | none |
| Vaccinated with *H. cerdo* digest and infected with *H. cerdo* | | | | | | |
| 02-3484 | 2840 | M | 1 | 1 | 1 | GEU - mild |
| 02-3485 | 3410 | M | 1 | 2 | 1 | possible GEU and ulcer |
| Unvaccinated and infected with *H. cerdo* | | | | | | |
| 02-3483 | 2970 | F | 1 | 3 | 1 | massive GEU, hemorrhage |
| 02-3486 | 3520 | M | 1 | 3 | 1 | small GEU |

$^a$Visually scored as 0 = no change from normal; +/− = possible change from normal; 1 = minimal change; 2 = moderate change; and 3 = severe change Isotype-specific ELISAs were performed in order to detect serum antibodies directed against *Helicobacter* species antigen in sera from *H. cerdo-* and *H. pylori*-infected pigs as described in Krakowka et al. (1987) *Infect. Immun.* 55:2789-2796; Krakowka et al. (1996) *Vet. Immunol. Immunopathol.* 55:2789-2796; and Eaton et al. (1992) *Gastroenterol.* 103: 1580-1586. The vaccine in saline alone without adjuvant or combined with the adjuvants described further below stimulated IgG isotype-specific antibodies. Moreover, sera from *H. cerdo*-infected and *H. pylori*-infected pigs cross-reacted in the ELISA when either bacterial antigen was used. See Tables 7-9.

2. The challenge dose of *H. pylori* inoculum was below the colonization threshold for gnotobiotic piglets, even though all vaccinates (proteolytic digest in squalene or saline, Groups A and Groups C) seroconverted after vaccinations (Pre-challenge sera) and ELISA titers had increased slightly by termination.

3. A "priming" effect of vaccination may be evident if the responses to the vaccine digests in either the squalene adjuvant or in saline (Groups A and C) is compared to the lack of response, even after subinfectious challenge, in the challenge control group (Group B).

TABLE 7

ELISA (IgG) serum antibody responses to lysates of *Helicobacter* species in gnotobiotic piglets vaccinated three times with *H. pylori* proteolytic digest, orally infected with a suboptimal amount of *H. pylori* and terminated at 24 days of age.

| Group/ Piglet No. | *Helicobacter pylori* antigen | | | *Helicobacter cerdo* antigen | | |
|---|---|---|---|---|---|---|
| | Pre-vaccination | Pre-challenge | Terminal | Pre-vaccination | Pre-challenge | Terminal |
| Group A: Vaccinated three times with Protease Digest in Squalene and challenged with *H. pylori* | | | | | | |
| 01-4161 | — | 0.86 | 1.02 | — | 0.74 | 0.81 |
| 01-4162 | — | 1.07 | 1.35 | — | 1.18 | 1.45 |
| 01-4163 | — | 1.02 | 1.25 | — | 0.92 | 1.05 |
| Group B: Vaccinated three times with saline alone and challenged with *H. pylori* | | | | | | |
| 01-4164 | — | — | — | — | — | — |
| 01-4165 | — | — | — | — | — | — |
| 01-4166 | — | — | — | — | — | — |
| Group C: Vaccinated three times with Protease Digest in saline and challenged with *H pylori* | | | | | | |
| 01-4167 | — | 1.10 | 1.23 | — | 1.01 | 1.21 |
| 01-4168 | — | 0.41 | 0.60 | — | 0.28 | 0.42 |
| 01-4169 | — | 1.19 | 1.16 | — | 1.05 | 1.12 |

Interpretation(s)

1. The ELISA OD values were corrected for background of roughly 0.1-0.2 OD units; there was no significant difference between *Helicobacter* sp antigens in ELISA assays.

TABLE 8

ELISA (IgG) serum antibody responses to lysates of *Helicobacter* species in gnotobiotic piglets orally infected with *H. cerdo* and terminated at 34 days of age.

| Group/ Piglet No. | *Helicobacter pylori* antigen | | | *Helicobacter cerdo* antigen | | |
|---|---|---|---|---|---|---|
| | Pre-vaccination | Pre-challenge | Terminal | Pre-vaccination | Pre-challenge | Terminal |
| 02-2662 | — | — | — | — | — | — |
| 02-2663 | — | — | — | — | — | — |
| 02-2664 | — | — | 0.23 | — | — | 0.25 |

Interpretation(s)

1. The ELISA OD values were corrected for background of roughly 0.1-0.2 OD units; there was no significant difference between *Helicobacter* sp antigens in ELISA assays.

2. Piglet 02-2663 was lightly colonized; organisms were only recovered in re-streaks; the other two piglets had colonization levels roughly one-tenth that (e.g. 105 cfu/gram) expected for *H. pylori*.

TABLE 9

ELISA (IgG) serum antibody responses to lysates of *Helicobacter* species in gnotobiotic piglets vaccinated three times with protease digests of either *H. pylori* or *H. cerdo*, challenged with *H. cerdo* after vaccinations and terminated at 35 days of age.

| Group/ Piglet No. | *Helicobacter pylori* antigen | | | *Helicobacter cerdo* antigen | | |
|---|---|---|---|---|---|---|
| | Pre-vaccination | Pre-challenge | Terminal | Pre-vaccination | Pre-challenge | Terminal |
| Group A: Vaccinated with *H. pylori* digest and infected with *H. cerdo* | | | | | | |
| 02-3481 | — | 1.23 | 1.29 | — | 1.20 | 1.18 |
| 02-3482 | — | 1.11 | 1.32 | — | 1.13 | 1.20 |
| Group B: Vaccinated with *H. pylori* digest and infected with *H. cerdo* | | | | | | |
| 02-3484 | — | — | 0.93 | — | 1.08 | 1.83 |
| 02-3485 | — | 1.15 | 1.84 | — | 0.65 | 1.44 |
| Group C: Unvaccinated and infected with *H. cerdo* | | | | | | |
| 02-3483 | — | — | 0.09 | — | — | 0.11 |
| 02-3486 | — | — | — | — | — | — |

Interpretation(s)

1. The ELISA OD values were corrected for background of roughly 0.1-0.2 OD units; there was no significant difference between *Helicobacter* sp antigens in ELISA assays.

2. Both digests stimulated both homologous and heterologous antibody production to specific *Helicobacter* sp antigens; there was no obvious difference in titers between homologous (same antigen for vaccination and antibody combination) and heterologous antigen (different antigen and antibody combination) ELISA systems.

3. The modest response to antigen in the challenge control piglets (Group C) is likely attributable to the fact that the challenge infection was for only 18 days (after vaccinations).

Example 4

Efficacy of Various Adjuvants

A number of experiments were conducted to test the efficacy of various adjuvants with the vaccine compositions, including incomplete Freund's adjuvant (ICFA) (Difco), TRIGEN oil-in-water adjuvant (Newport Laboratories, Worthington, Minn.), 1M-CREST 21 adjuvant (Newport Laboratories, Worthington, Minn.) and RESPISURE (containing an oil-in-water adjuvant) (Pfizer Animal Health). Pigs administered the vaccine adjuvanted with TRIGEN oil-in-water adjuvant showed a severe granulomatous reaction at injection sites but showed positive responses in 24-hour skin tests.

Seroconversion tests on pigs administered the TRIGEN oil-in-water adjuvant containing vaccine showed promise. Two out of three of the pigs administered the vaccine adjuvanted with IM-CREST 21 adjuvant died 48 hours after the first injection, likely due to LPS included in the adjuvant.

Parenteral vaccination using ICFA and RESPISURE (containing an oil-in-water adjuvant) prevented bacterial colonization and gastritis. However, parenteral vaccinations of actively infected piglets was not effective and may increase the histologic severity of gastritis. Therefore, antibiotic therapy could be administered prior to immunization of actively infected animals.

Immunogens in Squalene, RESPISURE (containing an oil-in-water adjuvant) and ICFA stimulated IgG isotype specific antibody responses prior to challenge. Immunogens in saline also stimulated antibody production but OD values were less than those given immunogen in adjuvants. Challenge infection with Hp/Hc increased OD values in terminal sera.

Further results are shown in Tables 10-16.

TABLE 10

A summary of histopathologic observations in gnotobiotic piglets vaccinated with protease digests in incomplete Freund's adjuvant, infected with *H. cerdo* and terminated at 35 days.

| Group/Piglet No. | Anatomical Region of the Stomach | | | | Nonglandular[a] Cardia | | | Gastric Lymph Nodes | Orgs. Present H/E |
|---|---|---|---|---|---|---|---|---|---|
| | Card. | Fund. | Antrum | Pylorus | Ero. | Ulc. | Other | | |
| *Vaccinated with H. pylori digest and infected with H. cerdo* | | | | | | | | | |
| 02-3481 | 2[b] | 0 | 1 | 0 | + | − | − | reactive | − |
| 02-3482 | 2 | 1 | 2 | 0 | + | − | − | reactive | − |
| *Vaccinated with H. cerdo digest and infected with H. cerdo* | | | | | | | | | |
| 02-3484 | 1 | 0 | 1 | 0 | + | + | − | reactive | − |
| 02-3485 | 3 | 0 | 2 | 0 | N/A | N/A | − | reactive | − |
| *Unvaccinated and infected with H. cerdo* | | | | | | | | | |
| 02-3483 | 2 | 0 | 4 | 1 | + | + | duoden. micro-ulcer[c] | reactive | +[d] |
| 02-3486 | 3 | 0 | 3 | 0 | + | + | − | reactive | − |

[a]Erosions (epithelial loss restricted to epithelium superficial to basement membrane) noted in the nonglandular cardia of the stomach. Ulcerative lesions of the nonglandular cardia penetrate the basement membrane, extend and into the muscularis. The ulcer bed consists of immature granulation tissue.
[b]Multifocal and follicular lymphocytic infiltrates into the gastric mucosa subjectively scored as 0 = no change from normal (no inflammation); 1 = minimal change from normal; 2 = moderate change from normal; 3 = severe change from normal and; 4 very severe change from normal.
[c]A micro-ulcer was detected in the duodenal mucosa of a section of duodenum present in this block. Tissues of the rest of the gastrointestinal tract were saved in formalin and will be examined.
[d]Organisms detected in the hematoxylin and eosin-stained section of the antrum adjacent to gastric follicular gastritis (Warthin Starry stained sections are pending).

TABLE 11

A summary of microbial culture and reisolation results in gnotobiotic piglets vaccinated with protease digests in incomplete Freund's adjuvant, infected with *H. cerdo* and terminated at 35 days.

| Group/Piglet No. | H. cerdo at termination (PID 35) | | Culture results in rest of gi tract[a,b] | | | | | | |
|---|---|---|---|---|---|---|---|---|---|
| | cfu/gm (× 10⁶) | Urease | Cata | Eso | Duo | Jej | Ileum | Sp Col | Dis Col | Ter Col |
| *Vaccinated with H. pylori digest and infected with H. cerdo* | | | | | | | | | |
| 02-3481 | 5.58 | + | + | − | − | − | − | − | − | − |
| 02-3482 | 2.17 | + | + | − | − | − | − | − | − | − |
| *Vaccinated with H. cerdo digest and infected with H. cerdo* | | | | | | | | | |
| 02-3484 | — | − | − | − | − | − | − | − | − | − |
| 02-3485 | 0.06 | + | + | − | − | − | − | − | − | − |
| *Unvaccinated and infected with H. cerdo* | | | | | | | | | |
| 02-3483 | 6.40 | + | + | − | + | + | + | − | − | − |
| 02-3486 | 33.20 | + | + | − | + | − | − | − | − | − |

[a]Abbreviations used: gi = gastrointestinal tract, Eso = esophagus, Duo = Duodenum, Jej = Jejunum, Sp Col spiral Colon, Dis Col = distal Colon, Ter Col = terminal Colon.
[b]reported as nd = not done, + = organisms present, − = organisms not present, (—) = no growth, even upon restreaks of the plates

TABLE 12

A summary of gross observations in gnotobiotic piglets vaccinated[a] with *H. cerdo* (Hc) proteolytic digest emulsified in ICFA and challenged with Hc 5 days after the last vaccination.

| Group/Piglet No. | Wt. (g) | Sex | Excess Mucus | Lymphoid Follicles | Submucosal Edema | Skin Test[b] 48 hr. | Ulcers and/or Erosions |
|---|---|---|---|---|---|---|---|
| *Uninfected (contact infected) Controls* | | | | | | | |
| 03-1100 | 1840 | F | 1[c] | 1 | 1 | −[d] | potential fundic mucosal ulcer, GEU |
| 03-1097 | 2100 | F | 1 | 2 | 1 | − | GEU (1 × 1 cm) |
| *Vaccinated 3x with Hc and then challenged with Hc* | | | | | | | |
| 03-1091 | 2050 | M | 1 | 1 | 1 | + | — |
| 03-1092 | 2590 | F | 1 | 2 | 1 | +/− | GEU and general congestion |

TABLE 12-continued

A summary of gross observations in gnotobiotic piglets vaccinated[a] with *H. cerdo* (Hc) proteolytic digest emulsified in ICFA and challenged with Hc 5 days after the last vaccination.

| Group/Piglet No. | Wt. (g) | Sex | Excess Mucus | Lymphoid Follicles | Submucosal Edema | Skin Test[b] 48 hr. | Ulcers and/or Erosions |
|---|---|---|---|---|---|---|---|
| 03-1093 | 2400 | F | 1 | 2 | 1 | − | small erosion? |
| 03-1094 | 1690 | M | 2 | 2 | 1 | +/− | — |
| 03-1095 | 2380 | M | 1 | 1 | 0 | − | — |
| 03-1096 | 2082 | M | 1 | 2 | 1 | +/− | — |

[a]Immunized at 7, 10 and 17 days of age with proteolytic Hc digest in incomplete Freunds adjuvant.
[b]Skin test antigen consisted of *H. cerdo* preparation, (10.0 ug, clarified sonicate in 0.1 ml PBS).
[c]Visually scored as 0 = no change from normal; 1 = minimal change; 2 = moderate change; and 3 = severe change
[d]Skin test responses scored as negative (−), positive (+) or +/− (reddening in the subcutis without obvious swelling.

TABLE 13

A summary of histopathologic changes in gnotobiotic piglets vaccinated[a] with *H. cerdo* (Hc) proteolytic digest emulsified in ICFA and challenged with Hc 5 days after the last vaccination.

| | Anatomical Region of the Stomach | | | | | | |
|---|---|---|---|---|---|---|---|
| Group/Piglet No. | Cardia | Fundus | Antrum | Pylorus | Duodenum | Gastric Lymph Nodes | Skin Test (24 hr.) |
| | Infected (challenge) Controls | | | | | | |
| 03-1100 | 2[b] deep ulcer | 1 | 2 | 0 | — | reactive | 2+ |
| 03-1097 | 2 deep ulcer | 1 | 2 | 1 | — | reactive | 2+ |
| | Vaccinated 3x with Hc and then challenged with Hc | | | | | | |
| 03-1091 | 2 (−) | 1 | 1 | 0 | — | reactive | 4+ |
| 03-1092 | 1 ulcer | 0 | 2 | 0 | — | reactive | 4+ |
| 03-1093 | 2 erosion | 1 | 2 | 0 | — | reactive | 4+ |
| 03-1094 | 0 (−) | 0 | 0 | 0 | — | reactive | 4+ PMNs/hem |
| 03-1095 | 1 erosion | 1 | 0 | 0 | — | reactive | 4+ PMNs |
| 03-1096 | 1 erosion | 0 | 1 | 0 | — | reactive | 1+ |

[a]Immunized at 7, 10 and 17 days of age with proteolytic Hc digest in incomplete Freunds adjuvant.
[b]Subjectively scored as 0 = no change from normal (no inflammation); 1 = minimal change from normal; 2 = moderate change from normal; and 3 = severe change from normal.

TABLE 14

A summary of microbiologic findings in gnotobiotic piglets vaccinateda with *H. cerdo* (Hc) proteolytic digest emulsified in ICFA and challenged with Hc 5 days after the last vaccination.

| Group/Piglet No. | *H. cerdo* at termination (PID 35) | | | Other |
|---|---|---|---|---|
| | cfu/gm (×10⁶) | Urease | Catalase | Microbial Contaminants |
| | Infected (challenge) Controls | | | |
| 03-1100 | 0.21 | + | + | none |
| 03-1097 | 6.61 | + | + | none |
| | Vaccinated 3x with Hc and then challenged with Hc | | | |
| 03-1091 | 0.16 | + | + | none |
| 03-1092 | 0.07 | + | + | none |
| 03-1093 | 0.93 | + | + | none |
| 03-1094 | — | − | − | none |
| 03-1095 | — | − | − | none |
| 03-1096 | 0.003 | + | + | none |

TABLE 15

ELISA (IgG) serum antibody responses to lysates of *Helicobacter* species in gnotobiotic piglets vaccinated three times with *H. pylori* proteolytic digest in either RESPISURER (containing an oil-in-water adjuvant) or incomplete Freund's adjuvant (ICFA), orally infected with *H. pylori* and terminated at 35 days of age.

| | *Helicobacter pylori* antigen | | | *Helicobacter cerdo* antigen | | |
|---|---|---|---|---|---|---|
| Group/ Piglet No. | Pre-vaccination | Pre-challenge | Terminal | Pre-vaccination | Pre-challenge | Terminal |
| *Group A: Vaccinated 3x with protease digest emulsified in Respisure and challenged with H. pylori* | | | | | | |
| 02-2021 | — | 1.13 | 1.45 | — | 0.98 | 1.34 |
| 02-2022 | — | 1.47 | 1.30 | — | 1.06 | 1.18 |
| 02-2023 | — | 1.14 | 1.40 | — | 1.23 | 1.47 |
| *Group B: Vaccinated 3x with protease digest in incomplete Freund's adjuvant and challenged with H. pylori* | | | | | | |
| 02-2024 | — | 1.26 | 1.89 | — | 0.80 | 1.39 |
| 02-2025 | — | 1.41 | 1.92 | — | 1.35 | 1.63 |
| 02-2026 | — | 1.34 | 1.64 | — | 1.42 | 1.44 |
| *Group C: Challenged with H. pylori* | | | | | | |
| 02-2027 | — | — | — | — | — | — |
| 02-2028 | — | — | 0.27 | — | — | 0.12 |

Interpretation(s)

1. The ELISA OD values were corrected for background of roughly 0.1-0.2 OD units; there was no significant difference between *Helicobacter* sp antigens in ELISA assays.

2. Both the RESPISURER (containing an oil-in-water adjuvant) and the ICFA adjuvant stimulated significant ELISA titers to *Helicobacter* sp antigens prior to challenge with *H. pylori*.

3. One of two unvaccinated control pigs challenged with *H. pylori* seroconverted; this "slow" serologic response has been seen in previous challenge experiments in that it takes several weeks to detect IgG antibodies and the challenge to termination interval was only 15 days.

TABLE 16

ELISA (IgG) serum antibody responses to lysates of *Helicobacter* species in gnotobiotic piglets vaccinated three times with *H. pylori* proteolytic digest, orally infected with a suboptimal amount of *H. pylori* and terminated at 24 days of age.

| | *Helicobacter pylori* antigen | | | *Helicobacter cerdo* antigen | | |
|---|---|---|---|---|---|---|
| Group/ Piglet No. | Pre-vaccination | Pre-challenge | Terminal | Pre-vaccination | Pre-challenge | Terminal |
| *Group A: Vaccinated 3x with saline alone and challenged with H. pylori* | | | | | | |
| 02-741 | — | — | — | — | — | — |
| 02-742 | — | — | — | — | — | — |
| 02-743 | — | — | — | — | — | — |
| *Group B: Vaccinated 3x with protease digest in saline and challenged with H. pylori* | | | | | | |
| 02-744 | — | 0.75 | 0.75 | — | 0.67 | 0.74 |
| 02-745 | — | 1.11 | 0.78 | — | 1.08 | 0.78 |
| 02-746 | — | 0.73 | 1.05 | — | 0.73 | 0.98 |
| *Group C: Vaccinated 3x with protease digest in TRIGEN adjuvant[a] and challenged with H. pylori* | | | | | | |
| 02-750 | | | | | | |
| 02-751 | | ELISAs in progress | | | | |
| 02-752 | | | | | | |
| *Group D: Vaccinated with protease digest in IM-CREST 21 adjuvant[a]* | | | | | | |
| 02-747 | — | died 48 hours after first vaccination | | | | |
| 02-748 | — | — | — | — | — | 0.25 |
| 02-749 | — | died 48 hours after first vaccination | | | | |

[a]Newport Laboratories, Worthington, MN

Interpretation(s)

1. The ELISA OD values were corrected for background of roughly 0.1-0.2 OD units; there is no significant difference between *Helicobacter* sp antigens in ELISA assays.

Example 5

Characterization of *H. cerdo* and *H. pylori*

In order to demonstrate that *H. cerdo* was in fact a distinct organism from *H. pylori*, SDS-PAGE gels were run under reducing conditions to examine the protein profiles of the two organisms. The stacking gel for separation consisted of 3.9% acrylamide; the separating gel contained 12% acrylamide. Each was made using standard procedures as outlined in *Current Protocols in Molecular Biology*, supplement 47, section 10.2A.6. In some instances, native PAGE gels were used that were purchased from BioRad Corporation. The gel loading buffer consisted of Tris-Cl (50 mM), pH 6.8, 2% SDS (electrophoresis grade), 0.1% bromophenol blue and 10% glycerol. Samples were run in a Tris-glycine buffer containing 25 mM Tris, 250 mM glycine (electrophoresis grade, pH 8.3) and 0.1% SDS.

The samples consisted of intact and digested *H. pylori* (Hp) and *H. cerdo* (Hc). The proteolytic digests were done as described above. One µl of each sample (2.4-3.0 µg) was diluted in distilled water to a final volume of 15 µl and diluted 1:2 with loading buffer. Samples were boiled for 3 minutes, and 20 µl of each sample loaded onto the gel. Samples (along with a standard) were then electrophoresed at 100 V for 60-75 minutes or until the dye fronts had just exited the gels. Gels were then stained with Coomassie Blue or silver stains to develop the separated bands and then photographed. Following clearing in dilute acetic acid solution overnight, gels were dehydrated and then photographed.

As shown in FIG. 1, the SDS-PAGE profiles of both intact and digested *H. pylori* and *H. cerdo* were different. The ">" in the figure illustrates bands present in Hp and absent from Hc. The "]" indicates low molecular weight protease digest products.

Figure 2:
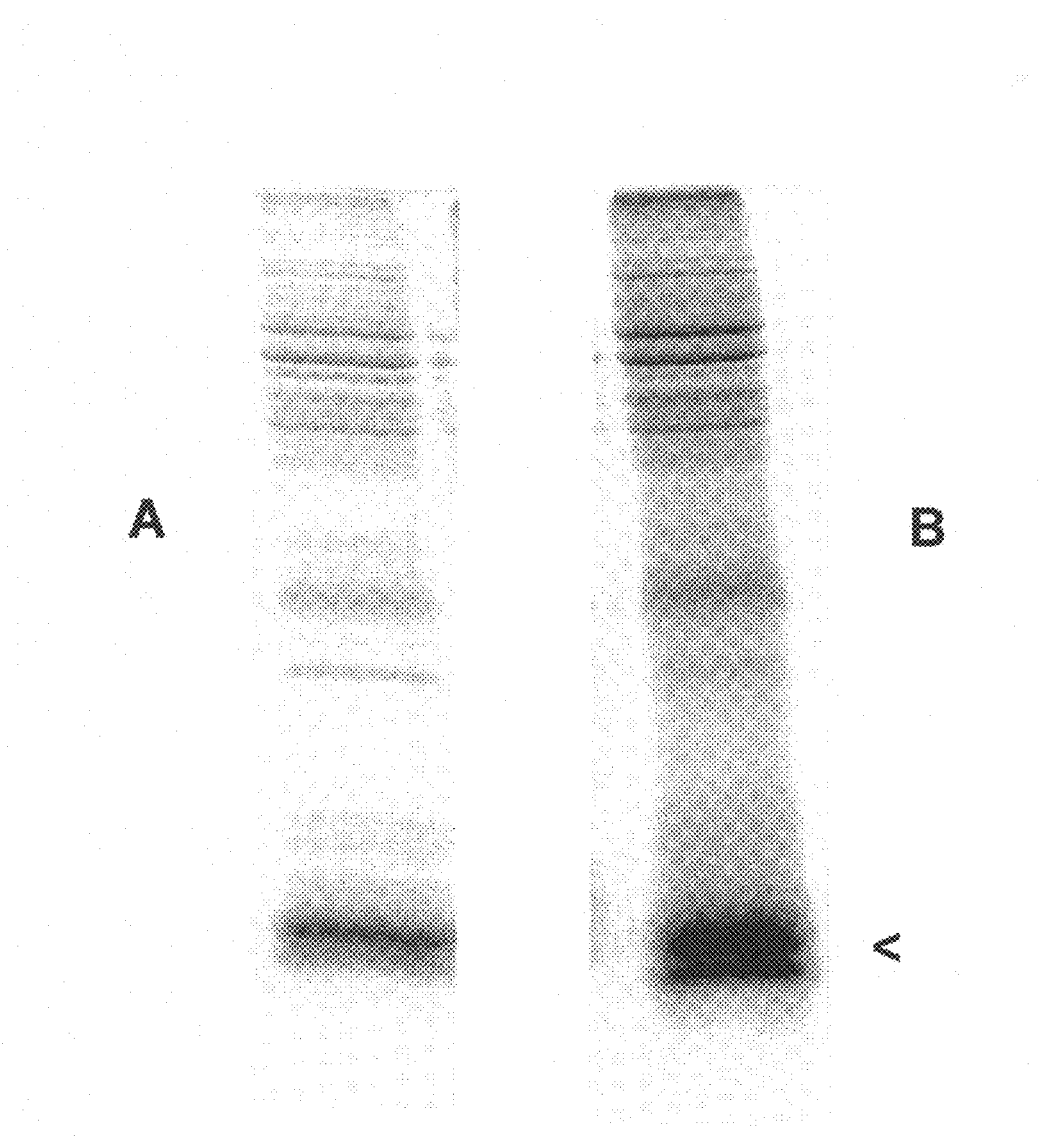

SDS-PAGE gels of intact and digested *H. cerdo* were also run and compared. As can be seen in FIG. 2A (intact) and 2B (digested), an increased amount of low molecular weight material was present in the proteolytic digestion product (indicated by "<" in FIG. 2B.

Western blot analysis of intact *H. cerdo* and digested *H. cerdo* was also performed. Samples were separated on PAGE gels (reducing and native gels, as described above) and were transferred to nitrocellulose membranes by standard electrophoretic methodology using a BioRad apparatus. Nitrocellulose membranes were incubated overnight (4° C.) in phosphate buffered saline containing 10% nonfat dry milk containing TWEEN 20 (polvoxvethylene-20-sorbitan monolaurate) (PBS-NFM) to block reactive sites on the membranes. After washing, a 1:250 dilution of porcine serum (diluted in PBS-NFM) was made and incubated for 2 hr at 22° C. After washing 3 times (5 minutes each) in PBS-NFM, membranes were incubated with goat anti-porcine IgG, for one hr at 22° C. The membranes were washed again as above and developed with warmed (37° C.) TMB membrane horse radish peroxidase substrate for several minutes. The reaction was stopped by the addition of excess distilled water. Membranes were then dried and photographed.

Figure 3:
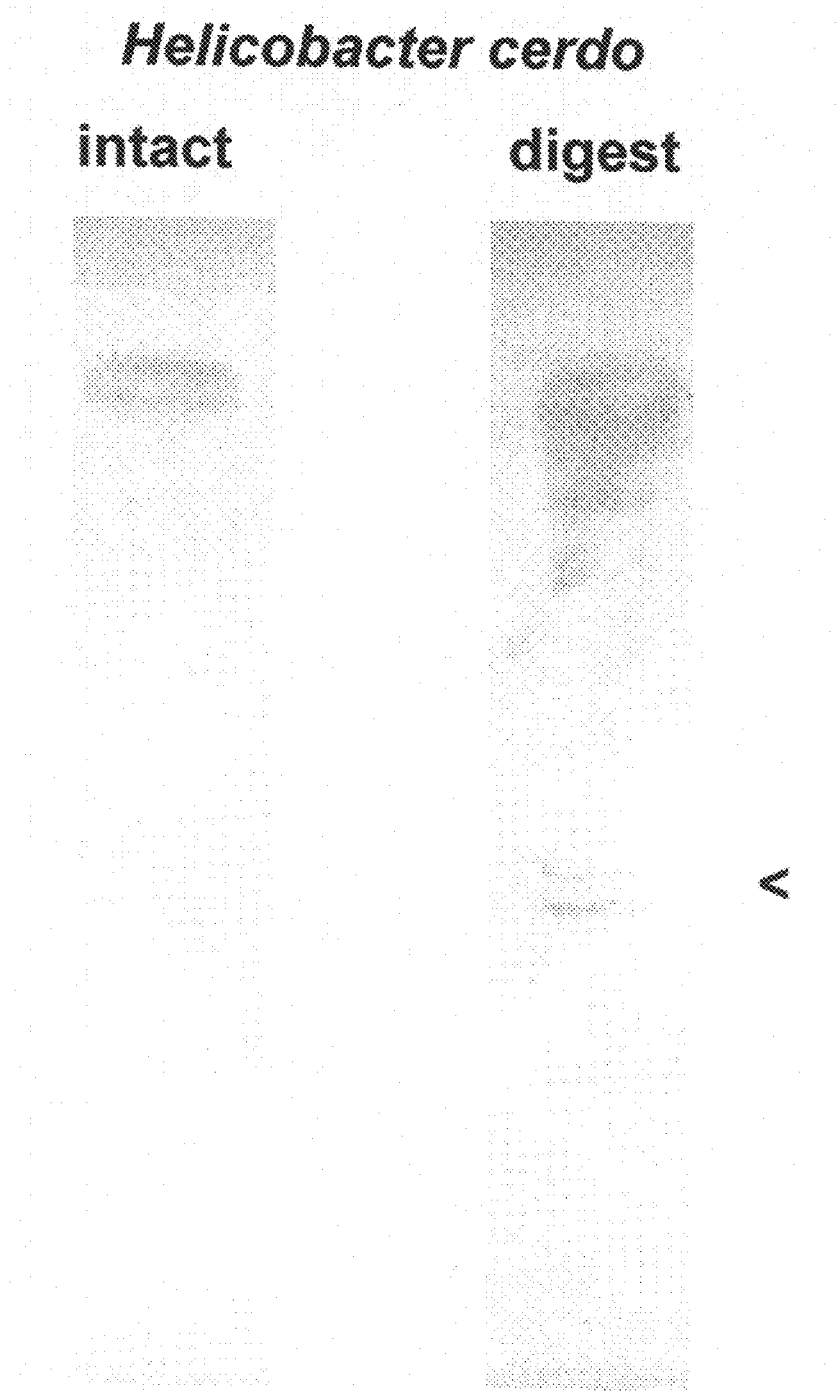
FIGS. 3A and 3B show a Western blot analysis of intact *H. cerdo* (3A) and an *H. cerdo* digest (3B) separated on a native, non-reducing gel.
Figure 4:
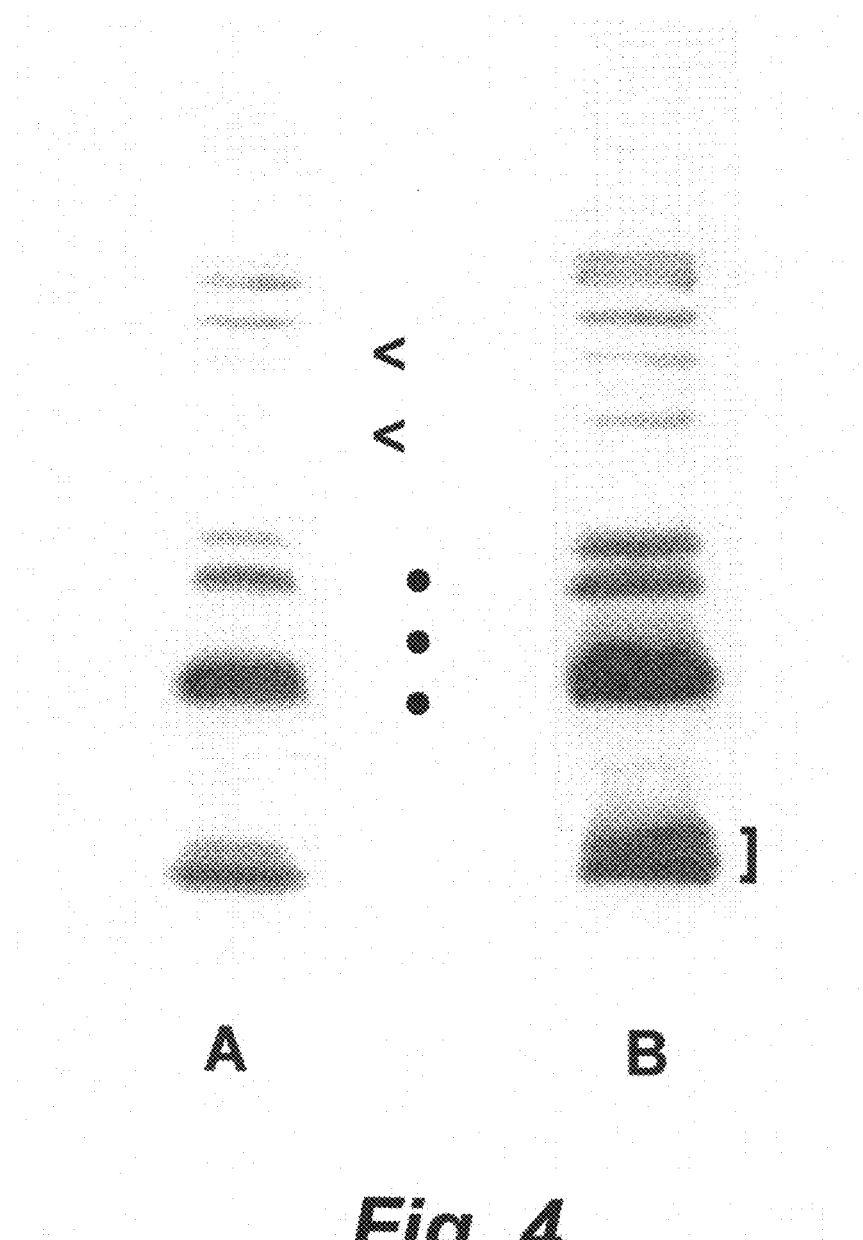
FIGS. 4A and 4B show a Western blot analysis of the antibody reactivity profile against intact *H. cerdo* (4A) and an *H. cerdo* digest (4B). An increased amount of low molecular weight material is seen in the digest (indicated by ]). Increased staining intensity is also seen (■), as well as additional immunoreactive bands (<).

As seen in FIGS. 3A and 3B, the low molecular weight material present in FIG. 2B enters the native gel and is immunoreactive with test sera from pigs. As shown in FIGS. 4A and 4B, Western blot analysis of the antibody reactivity profile against intact *H. cerdo* (4A) and an *H. cerdo* digest (4B) showed an increased amount of low molecular weight material in the digest (indicated by ]). Increased staining intensity was also seen (*), as well as additional immunoreactive bands (<). As is apparent, the *H. cerdo* lysate contains immunoreactive material that cross-reacts with the intact organism, indicating that this is likely the basis for protection. Moreover, prevaccination sera were negative and post-vaccination/post-challenge sera were strongly positive.

Example 6

Pathogenicity of *H. cerdo* Isolates in Swine as compared to *H. heilmannii*

In order to study the pathogenicity of *H. cerdo* in swine and compare this to that observed with *H. heilmannii*, the following experiment was conducted.

Materials and Methods

A. Gnotobiotic Piglets

A total 36 of gnotobiotic piglets from portions of 7 liffers were used in this study (Krakowka and Eaton "Helicobacter pylori infection in gnotobiotic piglets: A model of human gastric bacterial disease" in Advances in Swine in Biomedical Research II, Tumbleson et al., eds., Plenum Press, New York, N.Y., 779-810). In brief, piglets are derived from date-mated sows purchased from a local pork producer. After epidural anesthesia, a Caesarian section was performed and the gravid uterus exteriorized, severed from its abdominal attachments and entered into a transfer tank filled with chlorine disinfectant. The sows were immediately euthanatized by electrocution and exsanguination. Piglets were removed from the uterus, stimulated to breathe and, after resection of the umbilici, transferred into sterile pen-tub isolation units containing 6 separate partitions. Piglets were fed sow milk replacement diet (SIMILAC) with iron 3-4 times daily until termination at 35 days of age.

B. Isolation of *H. cerdo*

*H. cerdo* was isolated from porcine gastric mucosa as described in Example 1. Two isolates were obtained and termed "1268" and "2662" herein.

C. *H. heilmannii*

Pure cultures of *H. heilmannii* (Hh) were obtained from parietal cell suspensions initially recovered from Hh-infected nude mice as described in Eaton et al. "Isolation of Pure Populations of *Helicobacter heilmannii*-like bacteria" in *Campylobacters, Helicobacters and Related Organisms*, Newell et al., eds. (1996) Plenum Press, New York, N.Y., 25-31. In brief, Hh was separated from other bacterial species and microbial contaminants, by exploiting the affinity of Hh for the canalicular system of parietal cells. Isolated parietal cells were frozen in aliquots as starting material. The Hh isolate was passed twice in gnotobiotic mice using Hh-laden gastric homogenates which was confirmed by Warthin-Starry (WS) stains of cytospin preparations of the homogenates. A single passage of Hh was performed in gnotobiotic swine and the infectious inoculum was maintained by further passages of infected porcine gastric homogenates (10%, w/v) in gnotobiotic swine. The infectious homogenate was aliquoted into two ml volumes and frozen (−70 C) until used for in vivo studies.

D. Administration

For in vivo inoculations, isolates were expanded in Brucella broth. Each piglet received 2 ml of organisms (109 total) recovered during log phase growth orally at 3 days of age. As infection controls for some experiments, groups of gnotobiotic swine received 2 ml Brucella broth orally containing *H. pylori*, strain 26695 adapted for optimal growth in swine (Akopyants et al. (1994) Infect. Immun. 63:116-121) and similarly prepared. Uninfected control piglets received either Brucella broth alone or were not inoculated. To exclude inadvertent contamination between infection groups, each infection group was separately housed in gnotobiotic isolation units. The distribution of pigs by bacterial inoculation group was: 13 piglets from 4 different litters orally infected with isolate 2662 at 3 days of age, 5 piglets from one litter orally infected with isolate 1268 at 3 days of age and 6 piglets from one litter orally inoculated with Hh-containing gastric homogenates at 5 (n=3) and 21 days of age (n=3), 9 piglets from 4 litters orally infected with Hp, strain 26695 at 3 days of age and 3 piglets from 2 litters were used as uninfected controls.

E. Pathology 28 to 35 days after inoculation, a standardized procedure for sample collection evaluation of gastric tissues was used. Piglets, fasted for 12 hrs, were heavily sedated with ketamine HCl and removed from the isolation units. After collection of a terminal unclotted blood sample for serum, the piglets were euthanized with intravenous EUTHOL (sodium pentathol) solution. The stomachs were exteriorized, ligated at the esophagus and proximal duodenum and removed. The stomachs were aseptically opened by dissection along the greater and lesser curvatures and one-half of the stomach was excised for quantitative microbial culture (see below). Pertinent gross findings in the remaining one-half stomach (submucosal edema, amount of lumenal mucus, presence and extent of lymphoid follicles, and erosions or ulcers if present) were recorded and photographs of ulcerative lesions, if present, were taken. In the absence of ulcers, sections of the gastric cardia including the pars esophagea, flmdus, antrum and pylorus-proximal duodenum were collected for microscopic evaluation. Suspected ulcerative and erosive lesions in the pars esophagea and gastric mucosa were transected such that the surface containing the ulcers/erosions was available for microtome sectioning from the face of the paraffin blocks. Gastric samples were immersed in ten volumes of 10% phosphate-buffered formalin for at least 24 hrs prior to further processing. Formalin-fixed gastric mucosa samples were dehydrated in graded alcohols and processed for histopathology and embedded in paraffin blocks by standard methods. Five micrometer section replicates were stained with hematoxylin and eosin for morphologic evaluation, Warthin-Starry stains for organisms and with commercial rabbit anti-Hp-specific antisera by indirect immunohistochemistry essentially as described elsewhere (Krakowa and Eaton (2002) Vet. Immun. and Immunopathol. 88:173-182). To assess antigenic relationships recognized by infection-induced immune T cells, both 24 and 48 hr intradermal skin tests were performed in pigs by inoculation often micrograms of either or both Hp and 2662 sonicates in 100 microliters of saline into the external pinna of some of the swine.

F. Microbiology

Isolation units were screened for extraneous microbial contaminants after derivation and at intervals thereafter until termination by aerobic and anaerobic culture of swabs from feed pans, feces and isolation units. Bacterial contaminants were not identified. For preparation of in vivo inocula, Brucella broth, 2.8% w/v BACTO yeast extract (Difco Laboratories, Detroit, Mich. 48232) with 10% v/v fetal calf serum cultures in log phase growth was used. Bacterial enumeration was accomplished with a hemocytometer and counts adjusted to $10^8$ microbes per 2 ml per piglet. Assays for bacterial urease, catalase, oxidase and motility have been described elsewhere (Krakowka et al. (1987) Infect. Immun. 55:2789-2796; Krakowka and Eaton "Helicobacter pylori infection in gnotobiotic piglets: A model of human gastric bacterial disease" in Advances in Swine in Biomedical Research II, Tumbleson et al., eds., Plenum Press, New York, N.Y., 779-810). For quantitative determination of bacterial colony forming units (cfu) per gram of gastric mucosa recovered from infected piglets, the mucosa was separated from the underlying tunica muscularis, weighed, homogenized in 10% (w/v) Brucella broth, and 10-fold dilutions were plated in duplicate, onto blood agar or TVAP (Remel, Lenexa, Kans. 66315) agar plates and read after 4 days incubation 37 C, 10% $CO_2$, 5% oxygen and 85% nitrogen in 95% humidity. Porcine re-isolates were identified as Helicobacter species by Gram stain, colony morphology, urease and catalase enzyme activity and immunoreactivity with both monospecific Hp antisera collected from infected gnotobiotic swine and commercially available Hp-specific rabbit antisera (Novacastra: Vision Biosystems, 700 Longwater Dr., Norwell, Mass. 02061 and DAKO: Dakocytomation Calif., inc; 6392 Carpinterra, Calif. 93013).

Results

An occasional transient (24 hr) episode of anorexia was seen in a portion of Hp-infected gnotobiotic swine (Krakowka et al. (1987) Infect. Immun. 55:2789-2796; Krakowka and Eaton "*Helicobacter pylori* infection in gnotobiotic piglets: A model of human gastric bacterial disease" in *Advances in Swine in Biomedical Research II*, Tumbleson et al., eds., Plenum Press, New York, N.Y., 779-810). In the experiments described here, the infection of gnotobiotic swine with the porcine *Helicobacter* species was clinically asymptomatic and no overt differences in size, weight or demeanor was noted between these animals, the uninfected controls and the other animals on various experiments.

Gross lesions of gastric disease in infected pigs (GEU, glandular mucosal ulcers, lymphoid follicles, particularly along the lesser curvature, excess luminal mucus and mucosal edema) typical of *Helicobacter* species infections in gnotobiotic swine (Krakowka et al. (1987) Infect. Immun. 55:2789-2796; Krakowka and Eaton "*Helicobacter pylori* infection in gnotobiotic piglets: A model of human gastric bacterial disease" in *Advances in Swine in Biomedical Research II*, Tumbleson et al., eds., Plenum Press, New York, N.Y., 779-810; Krakowka et al. (1998) Vet. Pathol. 35:274-282; Krakowka et al. (1995) Infect. Immun. 63:2352-2355) were seen in the majority of 2662-infected and Hp-infected gnotobiotes (Table 17). Ulceration(s) of the pars esophagea (GEU) was seen in 9 of 13 piglets infected with 2662, 5 of 9 piglets infected with Hp and 1 of 5 piglets infected with isolate 1268. Neither the Hh-infected nor the uninfected controls developed GEU. In addition, small ulcers of the glandular gastric mucosa were seen in 4 of 13 2662-infected and one of five 1268-infected pigs but not in the control and the Hh infection groups. Enlargement of gastric lymph nodes were seen in many of the *Helicobacter* spp.-infected pigs as well.

Histologic findings confirmed that the GEU seen in the 2662- and Hp-infected piglets were erosive and ulcerative in nature. Penetrating ulcers of the gastric glandular mucosa, except for one 1268-infected piglet were found only in piglets orally inoculated with isolate 2662. In addition to gastric mucosal ulcers, micro-ulceration of the proximal duodenum was seen in one piglet of this infection group. Manifestations of gastric inflammation (lymphocytic and plasmacytic inflammatory cell infiltrates and mucosal lymphoid follicle formation) was most prominent in isolate 2662-infected piglets. These inflammatory lesions were most prominent in the lesser curvature of the stomach near the nonglandular cardia and in the antral mucosa, anterior to the gastric pylorus and distal to the fundus. Piglets infected with isolate 1268 and with Hh had minimal evidence of inflammation in gastric mucosa in that only 2 of 5 1268-infected piglets had any inflammatory cell infiltrates and none of these demonstrated lymphoid follicles. Gastric lymph nodes from many of the 2662 isolate- and Hp infected piglets were highly cellular and had developing lymphoid follicles suggestive of an induced local immune/inflammatory response in the stomachs of these animals. The remaining tissues were unremarkable.

All 13 piglets infected with isolate 2662 and three of nine piglets infected with Hp were used for quantitative recovery of bacteria. In the 2662-infected piglets, the level of infection varied from recovery after re-streaking (roughly equivalent to $10^3$ bacterial cfu/gram to greater that $6\times10^6$ bacterial cfu/gram. *Helicobacter*-like bacteria were recovered from one of five piglets inoculated with isolate 1268 and from none of the controls. No attempt was made to recover Hh from the Hh-inoculated swine.

The WS stain confirmed gastric infection with *Helicobacters*. Extracellular organisms consistent in morphology with Hp (small curved rods with occasional "gull wing" replicative forms) were identified in 12 of 13 piglets inoculated with isolate 2662 but not in tissues from 1268-infected pigs. In the former, the bacteria were most abundant in the gastric cardia, adjacent to the pars esophagea, the lesser curvature and the gastric antrum. Organisms were scarce or nonexistent in the fundus. All 6 piglets inoculated with Hh were WS-positive. Unlike Hp or isolate 2662, the Hh were easily distinguished by size (3-fold longer) and uniquely spiralled morphology. While some Hh microbes were found in the cardia, the vast majority of them were in the gastric pits of the fundus. Positive immunostaining for *Helicobacters* was obtained when replicate sections of 2662 infected gastric tissues were stained with rabbit anti-Hp antiserum immunohistochemistry (IHC) assay. Bacteria reacting with this reagent were identified in 12 or 13 piglets inoculated with isolate 2662, two of five piglets colonized by isolate 1268 and all six piglets infected with Hh. Bacteria staining with these reagents reacted weakly with isolate 1268. When compared to culture and re-isolation, both the WS and ICH methods for demonstration of bacteria were insensitive techniques and frequently scored as "negative" in stomachs which contain fewer than $10^6$ recoverable bacterial cfu per gram.

In five of the 2662-infected gnotobiotes, culture and reisolation of 2662 organisms was also performed in samples throughout (esophagus to rectum) throughout the gastrointestinal tract. Trace levels of 2662 were recovered in the proximal duodenum of two of these five and in the ileum and jejunum of one of the five piglets respectively; there were no histologic lesions in these tissues. Trace levels of *Helicobacter*-like organisms were recovered by culture from only one of five 1268-infected piglets. This culture-positive piglet had GEU, but not gastric mucosal ulcers. Since Hh is not culturable on artificial media, WS stains were relied on to confirm gastric colonization with this agent.

Terminal sera from all piglets were tested for homologous and heterologous antibodies to the *Helicobacters* by ELISA assays. All 13 sera from 2662 isolate-infected swine reacted to both Hp and 2662 antigens whereas none of the terminal sera from Hh- and isolate 1268-infected swine reacted with these same ELISA antigens. Convalescent sera from 1268-infected swine reacted only with 1268-origin ELISA antigen. A subset of pigs from each infection group was skin tested with either or both 10 micrograms of Hp sonicate or 2662 sonicate 48 hrs prior to termination. Histologic evaluation of skin test sites revealed dermal delayed type hypersensitivity responses to skin test antigens in four of five piglets inoculated with 2662, four of five piglets inoculated with isolate 1268 and seven of nine piglets infected with Hp when Hp sonicate was used. The dermis and subcutaneous tissues contained mononuclear cell infiltrates with a scattering of neutrophils and eosinophils typical of DTH responses to bacterial protein(s). The same four 2662 inoculated responded to 2662 sonicates as did five of six piglets infected with Hh. The immunologic and bacteriologic findings are summarized in Table 17.

Of the two isolates, it was evident that isolate 2662 was the most pathogenic. Isolate 2662 has been shown to be similar to human origin Hp (see Example 1). When compared to the other inoculation groups, piglets inoculated with 2662 had a higher incidence (70%) of erosions and ulcers of the gastric pars (GEU) than did those piglets infected with Hp (55%), isolate 1268 (20%) or Hh (0%). More importantly however was the incidence of ulceration in the glandular mucosa. While Hp, on occasion, will produce mucosal ulcers (Krakowka et al. (1995) *Infect. Immun.* 63:2352-2355), mucosal ulcers were seen in 5 of 13 (38%) colonized by isolate 2662. In addition, an ulcer in the proximal duodenum was seen in one of the pigs in this inoculation group. This incidence of true gastric mucosal ulceration was unexpected and exceeds that seen with Hp, a proven human and porcine gastric ulcerogen. It is noteworthy that Hh, a microbe associated with GEU and ulcer disease by others (Barbosa et al. (1995) *Vet. Pathol.* 32:134-139; Queiroz et al. (1996) *Gastroenterol.* 111:19-27; Melnichouk et al. (1999) *Swine Health Prod.* 7:201-205; Roosendaal et al. (2000) *J. Clin. Micorbiol.* 38:2661-2664) produced neither GEU or gastric mucosal ulceration in swine infected with this agent.

Like Hp infection in both humans and gnotobiotic swine, the developing inflammatory response in the gastric mucosa to gastric bacterial colonization was predominately lymphocytic in nature. Well developed lymphoid follicles in the antrum and cardia, distinct from the cardial Peyer's patches were regular features of gastritis. Significant infiltration with neutrophils, either in the mucosa or accumulations in the gastric pits, was not seen. While not quantitated, the intensity of the gastric cardial and antral inflammation was most evident in piglets inoculated with 2662 and least evident in the pigs infected with isolate 1268. As reported previously (Krakowka et al. (1998) *Vet. Pathol.* 35:274-282), Hh-associated nonsuppurative inflammation is modest in mono-infected gnotobiotes. Also like Hp infection in both humans and in gnotobiotic swine subsequently conventionalized (Bertram et al. (1991) *Rev. Infect. Dis.* 13:S714-S722; Krakowka and Eaton "*Helicobacter pylori* infection in gnotobiotic piglets: A model of human gastric bacterial disease" in *Advances in Swine in Biomedical Research II*, Tumbleson et al., eds., Plenum Press, New York, N.Y., 779-810), gastric infection by the *Helicobacters* appeared to be persistent in spite of a vigorous antibody- and T cell-mediated responses to bacterial antigens.

The above data evidences that gastric colonization with *H. cerdo* and *H. cerdo*-like gastric microbes may be critical factors in the initiation of porcine gastric ulcer disease. From this it follows that porcine GEU may ultimately be an infectious bacterial disease, rather than a disease produced by high carbohydrate diets and/or modern swine production methods. An ELISA serologic survey of over 1,000 serum samples from conventional swine of weanling to adult has shown that piglets begin the process of seroconversion to isolate 2662 antigen(s) at 5-6 weeks of age; by adulthood, over 80% of the pigs are IgG-isotype ELISA seropositive to Hp and isolate 2662. While it is possible that this high incidence of infection could, in part, be due to colonization and subsequent cross-reactivity with Hh, it is noteworthy that none of the gnotobiotic pigs infected with Hh here reacted in ELISA assays to Hp and isolate 2662 antigen, even when these sera were tested for activity using IgM isotype-specific secondary reagents. In a companion study, 2 faint bands were discerned by Western blot immunoassays when Hh convalescent sera was tested against Hp and isolate 2662.

such as *Bacillus* and *Lactobacillus* spp. (Krakowka et al. (1998) *Vet. Pathol.* 35:274-282) with the development of GEU under conventional management conditions remain to be delineated. If infectious components of porcine ulcer disease are established, then specific measures such as antimicrobial therapies, probiotics and vaccinations can be designed to prevent or control bacterial gastritis. In turn, this will provide producers with another method for control of porcine GEU and mucosal ulcer disease.

TABLE 17

A summary of pathologic and microbiologic findings in gnotobiotic piglets inoculated with porcine *Helicobacter* gastric isolates 2662 and 1268, Hh and Hp

| Pathologic and Microbiologic Feature | Isolate 2662 | Isolate 1268 | *H. pylori* strain 26695 | *H. heilmannii* 10% (w/v) homogenates | Uninfected controls |
|---|---|---|---|---|---|
| Pigs per group | 13 | 5 | 9 | 6 | 3 |
| Grossly evident mucosal ulcer(s) | 4/13[1] | 1/5 | 0/9 | 0/6 | 0/3 |
| Gross/histologically evident GEU of pars esophagea | 9/13 | 2/5 | 5/9 | 0/6 | 0/3 |
| Histologic mucosal micro-ulcers | 5/13 | 1/5 | 0/9 | 0/6 | 0/3 |
| Lymphocytic-plasmacytic mucosal inflammation | 13/13 | 2/5 | 8/9 | 5/6 | 1/3[2] |
| Antral lymphoid follicles, lesser curvature | 13/13 | 0/5 | 6/9 | 2/6 | 0/3 |
| Helicobacters by re-culture/isolation | 13/13 ($<10^3$ to $6.6 \times 10^6$) | 1/5 ($<10^3$) | 3/3 ($3.0 \times 10^4$ to $>6.0 \times 10^6$) | not attempted | 0/3 |
| Helicobacters by W/S stains | 12/13 | 0/5 | not done | 6/6 | 0/3 |
| Helicobacters by IHC stains | 9/9 | 2/5 | not done | 3/3 | not done |
| Seroconversion ELISA-Hp | 13/13 | 0/5 | not done | 0/6 | 0/3 |
| 48 hr. skin test response to Hp | 4/5 | 4/5 | 7/9 | note done | 0/3 |
| 48 hr. skin test response to 2662 | 4/5 | not done | not done | 5/6 | not done |

[1] number positive (numerator) versus the number examined (denominator)
[2] Focal lymphocytic inflammatory cell infiltrates seen in the cardia of one piglet The contributions of the diet to the pathogenesis of porcine GEU are undeniable (see Example 7 below and O'Brien J. J. Gastric Ulcers. *Diseases of Swine,* 6th ed. Editors A D Leman A D, et al., (1986), 680-691; Argenzio et al. (1996) *Am. J. Vet. Res.* 57:564-573). The evidence for gastric luminal acid-mediated damage to the pars is strong and the fact that the diet can be specifically manipulated to reduce the incidence of GEU argues strongly for the role that diet plays in promoting gastric ulcerogenesis. The general strategy for management of GEU and gastric mucosal ulceration is centered around prevention of acidic reflux into the pars by providing diets which are coarsely ground and by limiting fermentable carbohydrates (O'Brien J. J. Gastric Ulcers. *Diseases of Swine,* 6th ed. Editors A D Leman A D, et al., (1986), 680-691). This approach represents a compromise between providing a diet which promotes optimal growth and weight gain during the fattening period of production and prevention of GEU. The interactions of diet formulation, dietary carbohydrate content (chiefly as corn, cornstarch and corn byproducts) and the association of certain species of gastric microbes, both the *Helicobacters* and the carbohydrate-fermenting commensals Example 7

Production of an Animal Model of Porcine GEU

In order to produce an animal model for porcine GEU and compare this model to other potential models, the following experiment was conducted.

Materials and Methods

A. Gnotobiotic Piglets

A total of 22 gnotobiotic piglets from portions of 4 litters were used in these experiments. These were derived by Caesarian section and raised as described elsewhere (Krakowka and Eaton "*Helicobacter pylori* infection in gnotobiotic piglets: A model of human gastric bacterial disease" in *Advances in Swine in Biomedical Research II*, Tumbleson et al., eds., Plenum Press, New York, N.Y., 779-810). The basic diet for these piglets consisted of a sterile liquid sow milk replacement formula (SIMILAC) individually fed to each piglet in feed pans three times daily, 200-300 ml/feeding. The volume of diet was adjusted over time to accommodate the increased nutritional requirements of the growing piglets. Dietary supplementation with liquid carbohydrate was accomplished by adding sterile corn syrup (KARO) at 5% (v/v) at 5-7 days of age (Krakowka et al. (1998) *Vet. Pathol.* 35:274-282). This was increased to 10% (v/v) at 10-12 days of age and continued to termination at days 30-35 of age or when moribund (31 days of age in one instance).

B. Bacterial Inocula

*H. Heilmannii*: A total of 9 piglets in Group A were fasted for 12 hrs and then orally inoculated at 3 days of age with a murine gastric homogenate (Eaton et al. "Isolation of Pure Populations of *Helicobacter heilmannii*-like bacteria" in *Campylobacters, Helicobacters and Related Organisms*, Newell et al., eds. (1996) Plenum Press, New York, N.Y., 25-31) containing *H. heilmannii* (Hh) as described above and in Krakowka et al. (1998) *Vet. Pathol.* 35:274-282. No attempt was made to quantitate the number of infectious bacteria in this inocula since this agent is not culturable on conventional media.

*H. cerdo*: A total of 11 piglets (Group B), separately housed from Group A pigs above and the controls (Group C), were similarly inoculated with porcine *H. cerdo* ($10^8$ bacterial cfu contained in 2.0 ml Brucella broth) at 3 days of age, obtained as described above. Two piglets of Group C received Brucella broth alone as uninfected controls.

C. Experimental Design and Pathologic Evaluation

The basic design used in this study was similar to that described in Example 6 and in Krakowka et al. (1998) *Vet. Pathol.* 35:274-282. Separately housed piglet groups were fasted for 12 hrs and orally inoculated with bacteria at 3 days of age. Supplementation with carbohydrate into the diet was introduced gradually (5%) starting at 5 to 7 days of age and increased to 10% (v/v) when it appeared that the piglets had accommodated to this additive, usually by 10-14 days of age. Three Hh-infected piglets received carbohydrate supplementation as did 6 of the porcine *Helicobacter*-infected piglets. At planned termination at 30-35 days of age (post-infection days 27, 32), piglets were fasted overnight, sedated and removed from the isolation units. After collection of a terminal clotted blood sample for serum, piglets were euthanatized with an intravenous overdose of sodium pentothal (EUTHOL). The stomachs were isolated, ligated at the distal esophagus and proximal duodenum and removed. Using sterile methods, the stomach was opened along the greater and lesser curvatures.

When culture and re-isolation was performed, one-half of the stomach was used for microbiology as described in Example 6 and in Krakowka and Eaton "*Helicobacter pylori* infection in gnotobiotic piglets: A model of human gastric bacterial disease" in *Advances in Swine in Biomedical Research II*, Tumbleson et al., eds., Plenum Press, New York, N.Y., 779-810; Krakowka et al. (1998) *Vet. Pathol.* 35:274-282; and PCT Publication No. WO 2004/069184. For this, the mucosa was scraped free of the muscularis, weighed and then homogenized in Brucella broth as a 10% (w/v) suspension. Ten-fold dilutions of gastric homogenate were then plated in duplicate onto Skirrow's medium plates and these were incubated for 4 days, 37 C, 5% (v/v) oxygen. Re-isolates were confirmed to be *Helicobacter* species by colony morphology, Gram's stain and morphology and by biochemical tests for urease and catalase activity as described (Krakowka and Eaton "*Helicobacter pylori* infection in gnotobiotic piglets: A model of human gastric bacterial disease" in *Advances in Swine in Biomedical Research II*, Tumbleson et al., eds., Plenum Press, New York, N.Y., 779-810). In one instance, the GEU ulcer crater was dissected free of the surrounding gastric tissue and separately cultured for *Helicobacter*. As indicated above, no attempt was made to recover Hh from Group A piglets and the Warthin Starry stain was used to confirm gastric infection with this organism as described in Example 6 and in Krakowka et al. (1998) *Vet. Pathol.* 35:274-282.

For pathologic evaluation, all mucosal ulcers and GEU were photographed as fresh specimens before emersion fixation of the opened stomachs in 10% (v/v) phosphate-buffered formalin solution for 24 hrs. Representative sections of the nonglandular (esophageal) cardia, the glandular cardia, the fundus, the antrum, pylorus and proximal duodenum were collected, and processed into paraffin blocks by routine methods. Replicate 5 micron tissue sections were de-paraffinized through graded alcohols, rehydrated and stained with hematoxylin and eosin and Warthin Starry silver stains as described in Example 6 and in Krakowka and Eaton "*Helicobacter pylori* infection in gnotobiotic piglets: A model of human gastric bacterial disease" in *Advances in Swine in Biomedical Research II*, Tumbleson et al., eds., Plenum Press, New York, N.Y., 779-810 and Krakowka et al. (1998) *Vet. Pathol.* 35:274-282.

Results

As explained above, piglets infected with either of these gastric bacterial species and maintained with control milk replacement diet were clinically asymptomatic throughout the course of the experiments. Piglets which were fed milk replacement diet and added liquid carbohydrate were initially resistant to the diet but within several days consumed it completely between feedings as did their normal diet counterparts. Overnight (PID 30-31) one of the *Helicobacter*-infected piglets on high carbohydrate diet died. It was necropsied 6-8 hrs later.

At necropsy, the only extra-gastrointestinal lesion occurred in the livers of the carbohydrate-supplemented piglets. The livers were pale and somewhat yellow, compatible with fatty degeneration or glycogen infiltration. Table 18 summarizes the gross findings in the stomachs from the piglets in this experiment. As reported in Example 6 and in Krakowka and Eaton "*Helicobacter pylori* infection in gnotobiotic piglets: A model of human gastric bacterial disease" in *Advances in Swine in Biomedical Research II*, Tumbleson et al., eds., Plenum Press, New York, N.Y., 779-810; Krakowka et al. (1998) *Vet. Pathol.* 35:274-282; PCT Publication No. WO 2004/069184; and Krakowka et al. (1987) *Infect. Immun.* 55:2789-2796, gnotobiotic swine persistently infected with gastric *Helicobacters* develop gastric inflammation grossly evident as the lymphoid follicle development, predominately in the lesser curvature of the stomach and the antrum. Accompanying this is mild and variable submucosal edema of the gastric lamina propria (Krakowka and Eaton "*Helicobacter pylori* infection in gnotobiotic piglets: A model of human gastric bacterial disease" in *Advances in Swine in Biomedical Research II*, Tumbleson et al., eds., Plenum Press, New York, N.Y., 779-810). These manifestations of gastritis were not present in the uninfected control pigs but were detected in all but one of the infected pigs, regardless of the species of *Helicobacters* present. Small ulcers in the glandular gastric mucosa were detected in 3 of 11 piglets infected with porcine *H. cerdo* and in none (0 of 9) piglets infected with Hh. These mucosal ulcers were similar to those described in Example 6. Erosive lesions in the nonglandular pars esophagea are seen occasionally in *H. pylori*-infected swine (Krakowka and Eaton "*Helicobacter pylori* infection in gnotobiotic piglets: A model of human gastric bacterial disease" in *Advances in Swine in Biomedical Research II*, Tumbleson et al., eds., Plenum Press, New York, N.Y., 779-810); these lesions were also detected in 2 of 9 Hh-infected piglets.

Extensive and deep ulceration of the pars esophagea, morphologically indistinguishable from naturally occurring porcine GEU in conventional swine (O'Brien J. J. Gastric Ulcers. *Diseases of Swine,* 6th ed. Editors A D Leman A D, et al., (1986), 680-691; Embaye et al. (1990) *J. Comp. Path.* 103: 253-264) was present in all six piglets infected with porcine *Helicobacter* species and fed a diet supplemented with fermentable carbohydrate. In these swine, the ulceration was deep, extensive and included the entire body of the gastric pars esophagea in 4 of these piglets and were 1.5 to 2.0 inches in diameter. In two piglets, gastric serosal edema was present in the serosa exterior to the GEU. The ulcer bed in 4 of 6 piglets contained necrotic debris, gastric mucus and partially digested blood, indicating that the ulcerative process had progressed beyond the lamina propria to involve the underlying muscularis mucosa. The cause of death in the piglet found dead was exsanguination into the stomach. In that piglet, the stomach was three-fold larger than expected and filled with clotted and partially digested blood and mucus. The spleen was severely contracted and the outside the stomach was thin, watery and unclotted. That this ulcerative process had been present for at least several days prior to termination in this piglet group was suggested by the presence of melena in the small and large intestine in 4 of the 6 piglets.

Histologic findings in the stomach confirmed the presence of lymphoid follicles embedded in the gastric mucosa. As well, a moderate, predominately lymphocytic inflammatory infiltrate in the mucosa accompanied follicle development. Both of these features are regular findings in swine infected with gastric *Helicobacters* (Krakowka and Eaton "*Helicobacter pylori* infection in gnotobiotic piglets: A model of human gastric bacterial disease" in *Advances in Swine in Biomedical Research II,* Tumbleson et al., eds., Plenum Press, New York, N.Y., 779-810). The ulcerative lesions in the pars were histologically comparable to those described in conventional swine by others (O'Brien J. J. Gastric Ulcers. *Diseases of Swine,* 6th ed. Editors A D Leman A D, et al., (1986), 680-691; Embaye et al. (1990) *J. Comp. Path.* 103:253-264). The ulcer beds were devoid of epithelial cells and consisted of granulation tissue, hemorrhage and necrotic debris. Inflammatory cells which accompanied these lesions were predominately dead and dying neutrophils. The edges of the ulcer contained hyperplastic remnants of nonglandular epithelium, inflammatory cell infiltrates and were distended by serous fluid accumulations.

None of the Hh-infected swine were cultured for recovery of *Helicobacters* as this agent was unculturable. Four of six *H. cerdo*-infected piglets fed supplemental carbohydrate were cultured for quantitative recovery of *Helicobacters.* Bacterial colony forming units (cfu) per gram of gastric mucosa ranged from 0.14 to $8.16 \times 10^6$, values typical for gnotobiotes persistently infected with either *H. pylori* (Krakowka and Eaton "*Helicobacter pylori* infection in gnotobiotic piglets: A model of human gastric bacterial disease" in *Advances in Swine in Biomedical Research II,* Tumbleson et al., eds., Plenum Press, New York, N.Y., 779-810) or porcine *H. cerdo* species (see Example 6). In one of these piglets, the ulcer crater was dissected free of the surrounding gastric mucosa and cultured separately. The ulcer contained $0.2 \times 10^6$ bacterial cfu whereas the remaining glandular mucosa in that pig yielded ten-fold more organisms ($2.94 \times 10^6$ cfu/gram).

The Warthin-Starry silver stain was used to confirm gastric colonization in all pigs. All nine Hh infected swine contained readily detectible microbes of characteristic tightly spiralled morphology (see Example 6 and Krakowka et al. (1998) *Vet. Pathol.* 35:274-282). In these pigs, the bulk of the organisms were detected in the gastric fundus and antrum in extracellular locations associated with the lumenal surface epithelium or within the lumens of gastric pits. As described above, the gastric mucosal cardia and antrum, particularly along the lesser curvature, was regularly colonized by short curved rod-shaped microbes of typical *Helicobacter* morphology. Organisms were abundant in the superficial mucus layer and adherent to the gastric glandular mucosa adjacent to the ulcerative lesions in the pars. However, organisms were not detected in the ulcer craters in the pars.

To summarize, severe and life-threatening ulcers of the porcine pars esophagea were produced in all gnotobiotic swine persistently colonized with porcine *H. cerdo* when a readily fermentable source of dietary carbohydrate was added to the sterile milk diet. These experimentally produced GEU are indistinguishable from naturally occurring GEU in conventional swine. While mild erosive lesions in the pars are occasionally detected in gnotobiotic piglets colonized with *H. pylori* (Krakowka and Eaton "*Helicobacter pylori* infection in gnotobiotic piglets: A model of human gastric bacterial disease" in *Advances in Swine in Biomedical Research II,* Tumbleson et al., eds., Plenum Press, New York, N.Y., 779-810), *Lactobacillus* sp. and *Bacillus* sp. fed sow milk replacement diet (Krakowka et al. (1998) *Vet. Pathol.* 35:274-282), these lesions are mild, do not progress to ulceration and have never been associated with deaths in the isolation units. Importantly, colonization of liquid carbohydrate-supplemented gnotobiotes with Hh in both the present study and in a previously reported study (Krakowka et al. (1998) *Vet. Pathol.* 35:274-282), did not produce GEU. These data strongly implicate porcine *H. cerdo* species and not Hh in the genesis of significant GEU disease in swine.

Indeed, the data here and elsewhere (Krakowka et al. (1998) *Vet. Pathol.* 35:274-282) suggest that the association between gastric Hh colonization and GEU is coincidental, not causal. This does not appear to be the case with the newly identified porcine gastric *H. cerdo* species described above. Unlike mono-colonization with Hh as described herein and in Krakowka et al. (1998) *Vet. Pathol.* 35:274-282, and even *H. pylori* (Krakowka et al. (1995) Infect. Immun. 63:2352-2355; Krakowka and Eaton "*Helicobacter pylori* infection in gnotobiotic piglets: A model of human gastric bacterial disease" in *Advances in Swine in Biomedical Research II,* Tumbleson et al., eds., Plenum Press, New York, N.Y., 779-810), gastric colonization with this bacterial species is associated with a high incidence of GEU (70%) and gastric and duodenal glandular mucosal ulceration (40%) when piglets are maintained on control milk replacement diet. In the present experiments, ulcers in the gastric glandular mucosa were identified in 2 of 5 infected swine on control diet. More importantly however, was the combined influence of persistent gastric colonization with this bacterial species and a readily available source of dietary carbohydrate upon the incidence and severity of GEU. All six *H. cerdo*-infected piglets which received carbohydrate supplementation developed severe and life threatening GEU disease. In fact, one piglet died overnight on PID 30-31 without demonstrating definitive clinical signs of gastric ulceration prior to death. Sudden death is a typical clinical finding in feeder swine GEU (O'Brien J. J. Gastric Ulcers. *Diseases of Swine,* 6th ed. Editors A D Leman A D, et al., (1986), 680-691). Moreover, three other piglets in this group had obvious evidence of intra-gastric bleeding (partially digested blood in the ulcer crater and adhered to the gastric luminal mucus layer) which had been occurring for at least a day as evidenced by the melena present in the small and large bowel.

As described above, the preferred gastric niche for this bacterial agent is the lesser curvature of the gastric cardia and the antrum. The former is immediately adjacent to the pars esophagea and, unlike Hh, this anatomical proximity provides strong circumstantial evidence for intimate causality. In this regard, it is important to stress that this *Helicobacter* species, like *H. pylori*, does not adhere to the stratified squamous epithelium of the pars nor does it colonize the pars esophageal region directly. Rather, the gastric colonization pattern in gnotobiotes is identical to that seen with *H. pylori*. For *H. pylori*, colonization sites appear to be dictated by surface expression of glycoprotein residues which interact with reciprocal carbohydrate residues (Lewis antigens) in gastric mucus and gastric epithelia. Lewis antigenic arrays in humans are also expressed in swine and, without being bound by a particular theory, the ease whereby gastric *Helicobacter* species initiate and perpetuate gastric colonization in swine may be because of this molecular mimicry phenomenon.

As shown above, neither excess dietary carbohydrate nor bacterial infection alone produced GEU. Rather, it appears that the combination of a carbohydrate-rich diet along with colonization by *H. cerdo* act synergistically to promote both the incidence and severity of GEU. The demonstration that porcine-origin gastric *Helicobacter* species such as *H. cerdo* are intimately involved in the development of GEU as shown above has several implications for the management of this disease and this bacterial infection in conventional swine. Innovative anti-microbial approaches to the control or prevention of gastric infection by these *Helicobacters* may be merited in the control and management of porcine GEU and vaccine compositions to prevent *H. cerdo* infection, such as *H. cerdo* and *H. pylori* vaccines, will also be useful.

18:711-719. In particular, suspensions of *H. cerdo* or *H. pylori* bacteria propagated in liquid cultures of Brucella broth (Difco) supplemented with 10% fetal bovine serum (B-FBS) under microaerophilic conditions were allowed to reach approximately $10^9$ bacteria per ml. The bacteria were recovered by centrifugation (2000-3000×g) for 10 minutes. The spent supernatant was discarded and the bacterial pellet was resuspended in a minimal amount of Dulbecco's phosphate-buffered saline, transferred to a plastic cryo vial and frozen at −70 degrees C. While frozen, the bacterial pellet was lyophilized in a centrifugal evaporator apparatus (speed vac). Lyophilized bacterial pellets were pooled and weighed. For bacterial digestion, pepsin (Sigma, St. Louis, Mo.) at a concentration of 1.0 μg/ml was prepared by dilution into 10 mM HCl, pH 1.9-2.2. 1 μg of pepsin was incubated with 1 mg of lyophilized bacteria for 24-25 hours at 37 degrees C. on a magnetic stirrer. After completion of digestion, the digest was aliquoted into 1 ml doses, labeled and frozen at −70 degrees C. until use. FIG. 1 shows the proteolytic enzyme digest profiles of *H. cerdo* and *H. pylori*.

B. Vaccination and Challenge Protocol

The lysates were formulated into vaccine compositions and used to vaccinate gnotobiotic pigs as follows. The lysates were diluted to 24-25 mg/ml in Dulbecco's phosphate-buffered saline and mixed with 1 ml of incomplete Freund's

TABLE 18

A summary of gross findings in the stomachs of gnotobiotic swine infected with gastric *Helicobacters* with or without dietary supplementation with liquid carbohydrate.

| Infection/ Treatment Group | Gastric Mucosal Lymphoid Follicles | Gastric Mucosal Edema | Ulcers in Glandular Mucosa | Erosions of Pars Esophagea | Ulceration of Pars Esophagea | Gastrointestinal Hemorrhage (melena) |
|---|---|---|---|---|---|---|
| Uninfected Controls (n = 2) | | | | | | |
| 0/2[a] | 0/2 | 0/2 | 0/2 | 0/2 | | 0/2 |
| Infected with H. heilmannii (14 and 25 days) and fed normal diet (n = 6) | | | | | | |
| 6/6 | 6/6 | 0/6 | 1/6 | 0/6 | | 0/6 |
| Infected with porcine *H. heilmannii* (25 days) and fed normal diet supplemented with carbohydrates (n = 6) | | | | | | |
| 3/3 | 3/3 | 0/3 | 1/3 | 0/3 | | 0/3 |
| Infected with porcine *Helicobacter* species (25 days) and fed normal diet (n = 5) | | | | | | |
| 5/5 | 3/5 | 3/5 | 2/5 | 0/5 | | 0/5 |
| Infected with porcine *Helicobacter* species (25 days) and fed normal diet supplemented with carbohydrates (n = 6) | | | | | | |
| 6/6 | 6/6 | 0/6 | 1/6 | 5/6 | | 4/6 |

[a]incidence = number positive (numerator) versus total number (denominator)

Example 8

Infectivity and Protective Capability of *Helicobacter* Species

In order to determine the infectivity and protective capability of *H. cerdo*, *H. pylori* and *H. heilmannii*, the following experiments were conducted.

Materials and Methods

A. Preparation of *H. cerdo* and *H. pylori* Lysates

*H. cerdo* and *H. pylori* lysates were prepared using proteolytic digestion, according to a method similar to the digestion protocol described in Waters et al. (2000) *Vaccine* adjuvant. The vaccine was emulsified in adjuvant and the mixture was injected into the dorsal axillas and hips of each piglet. Each piglet received 3 injections at 3, 10 and 17 days of age.

Vaccinated pigs and unvaccinated controls were orally inoculated with *H. cerdo* organisms (roughly $10^8$ to $10^9$ colony forming units (cfu) in 2.0 ml of inoculum) 7 to 10 days after the last vaccination. The pigs were terminated 10-14 days after challenge and efficacy of the vaccination was determined by a combination of gross and histologic examination of the stomachs and by quantitative re-culture of the challenge inoculum from gastric mucosa as described in Example 6.

C. Cutaneous Delayed-Type (48 hr) Skin Test Responses

Gnotobiotic swine mono-infected with either *H. pylori* or *H. cerdo* were skin-tested by intradermal injection of 100 microliters of a skin test reagent containing 10 micrograms of bacterial lysate (either *H. cerdo* or *H. pylori*). Skin test sites were biopsied and examined at 24 and 48 hours after skin test and the histology of the skin test sites was determined by microscopic examination of tissue sections.

D. Indices of Efficacy

The efficacy of proteolytic digestion was assessed by SDS-PAGE electrophoretic separation and analysis of the protein bands produced by digestion (in comparison to the SDS-PAGE profiles of undigested bacteria). A successful digestion resulted in the appearance of low molecular weight proteins in the digest which were absent in the undigested intact organism.

The in vivo safety of the vaccine preparations was determined in uninfected gnotobiotic swine. For this, vaccine digests were administered as above and clinical evidence for endotoxin-mediated damage (diarrhea, hypovolemic shock, respiratory distress and sudden death) were monitored. All preparations were judged as "safe" by this process.

The efficacy of the vaccine preparations in inducing both humoral and cellular immune responses in vaccinates was determined by an ELISA assay for IgG and/or IgM antibodies to undigested *H. cerdo* cell lysates in post-vaccinal sera and by 48 hour intradermal cutaneous skin test responses to *H. cerdo* lysate. Delayed-type dermal hypersensitivity was confirmed by histologic examination of the skin test sites and demonstration of lymphocytic-plasmacytic and monocytic cellular infiltrates into the skin test sites.

The vaccine digest was considered to be effective if the process of vaccination eliminated recoverable bacteria from gastric homogenates or reduced bacterial cfu an average of 2 logs below the challenge control pigs. Additional parameters of success included reduced or absent gastric inflammation (gastritis) and the absence of either gastric mucosal ulcers or ulcers of the pars esophagea.

Results

Tables 19-22 summarize the results of the experiments. Western blot analyses of pooled convalescent sera from *H. pylori*-infected and *H. cerdo*-infected swine exhibited extensive IgG-based cross-reactivities to multiple proteins. Mono-infection with either bacterium induced a modest lymphocytic and monocytic infiltration into the sites by 30-35 days after infection when tested with either *H. pylori* or *H. cerdo* skin test preparations. Parenteral vaccinations with *H. pylori* and *H. cerdo* bacterial digests induced the same response.

When piglets were parenterally vaccinated and then skin tested with these antigens at termination, enhancement of the degree and amount of inflammatory cell infiltrates were seen. There was no detectible difference between skin test sites induced by *H. pylori* lysate and skin test sites induced by *H. cerdo* lysate.

One small (n=2 piglets) heterologous protection trial in swine was attempted. In that trial, two piglets were vaccinated with a freshly prepared *H. pylori* proteolytic digest and then challenged by oral inoculation with *H. cerdo*. Surprisingly, a reduction in recoverable bacterial cfu from the stomach was not seen. There are several explanations for this result. First, an insufficient number of piglets were used in this trial. Protection may well have been seen in some fraction of the challenged piglets had larger numbers of challenge animals been involved. Second, the *H. pylori* digest may have been immunologically defective in this trial. That is, a parallel homologous trial (e.g. vaccination with that *H. pylori* digest and challenge with *H. pylori*) was not conducted to determine if the test vaccine product was effective. Other studies presented in the accompanying tables, and other Examples, have documented the fact that *H. pylori* vaccine digest preparations, if properly prepared, provided protection to piglets when challenged with *H. pylori* bacteria. Finally, the challenge inoculum of *H. cerdo* used in this experiment used roughly ten-fold more bacteria ($10^9$ cfu) to challenge the two vaccinates than ordinarily used (roughly $10^8$ cfu) in protection and challenge studies. In this case, any protective effects of vaccination would be obscured in the face of an overwhelming bacterial challenge.

The data presented in the above examples, show that *H. pylori* and *H. cerdo* possess the common features characteristic of the *Helicobacter* genus. These include the following characteristics held in common: Gram negative, short curved rods, microaerophilic growth pattern, urease enzyme activity, catalase enzyme activity and possession of the gene cluster referred to as the "cagA pathogenicity island." Additionally, there is a strong homology between the protein profiles (similar number of proteins with similar electrophoretic mobilities) of *H. pylori* and *H. cerdo* as evidenced by SDS-PAGE analysis (see, FIGS. 5A and 5B) and a significant degree of immunological cross-reactivity between the two *Helicobacter* species. Thus, given adequate conditions and effective digests, it would be expected that *H. pylori* digests or fractions thereof would provide a measure of immunoprotection in species (swine and others) which are susceptible to infection with their own homologous *Helicobacter* species (*H. cerdo* in swine, for example).

TABLE 19

Summary of single agent infection studies.

| Challenged with: | n/group | No. positive/ total cultured | Mean cfu of infected pigs | Mean cfu of total group |
|---|---|---|---|---|
| H. cerdo | 13 | 10/10 | $7.06 \times 10^6$ | $7.06 \times 10^6$ |
| H. pylori | 5 | 4/5 | $0.82 \times 10^6$ | $0.66 \times 10^6$ |
| H. heilmannii | 6 | 5/6 | not culturable | |
| H. cerdo and H. heilmannii | 3 | 3/3 | Trace levels of *H. cerdo* recovered; all were WS-positive for *H. heilmannii* | |

TABLE 20

Summary of vaccinations with *H. cerdo* digest upon homologous and heterologous protection.

| Challenged with: | n/group | No. positive/ total cultured | Mean cfu of infected pigs | Mean cfu of total group |
|---|---|---|---|---|
| *H. cerdo* | 8 | 4/8 | $0.3 \times 10^6$ | $0.15 \times 10^6$ |
| *H. pylori* | | | | |
| *H. heilmannii* | 9 | 7/9 WS-positive | not culturable | |

TABLE 21

Summary of vaccinations with *H. pylori* digest upon homologous and heterologous protection.

| Challenged with: | n/group | No. positive/ total cultured | Mean cfu of infected pigs | Mean cfu of total group |
|---|---|---|---|---|
| *H. cerdo* | 2 | 2/2 | $3.90 \times 10^6$ | $3.90 \times 10^6$ |
| *H. pylori* | | 3/8 | $0.29 \times 10^6$ | $0.03 \times 10^6$ |
| *H. heilmannii* | 8 | | | |

TABLE 22

Summary of serologic cross-reactions between porcine *Helicobacter* species as determined with pooled convalescent sera tested in ELISA and Western blot immunoassays and skin test reactions (48 hour intradermal injections into the pinna prior to termination.

| Challenged with: | Serology (ELISA) | | Western Blot analysis | | Intradermal skin test | |
|---|---|---|---|---|---|---|
| | *H. cerdo* | *H. pylori* | *H. cerdo* | *H. pylori* | *H. cerdo* | *H. pylori* |
| *H. cerdo* | + | + | many bands | many bands | ++ | ++ |
| *H. pylori* | + | + | many bands | many bands | +/− | ++ |
| *H. heilmannii* | − | − | +/− | +/− | + | +/− |

Thus, animal models for the study of *Helicobacter* infection and methods for treating, preventing and diagnosing *Helicobacter* infection are described, as well as compositions for use with the methods. Although preferred embodiments of the subject invention have been described in some detail, it is understood that various modifications and variations can be made without departing from the spirit and the scope of the invention as defined by the claims. Such modifications and variation will be apparent to those skilled in the art.

We claim:

1. A method of eliciting an immunological response against *Helicobacter* in a porcine subject comprising administering to the subject a therapeutically effective amount of a composition comprising a *Helicobacter* porcine gastric isolate lysate.

2. The method of claim 1, wherein the composition further comprises an adjuvant.

3. The method of claim 1, wherein the composition is administered parenterally.

* * * * *